United States Patent [19]

Theofan et al.

[11] Patent Number: 5,420,019
[45] Date of Patent: May 30, 1995

[54] STABLE BACTERICIDAL/PERMEABILITY-INCREASING PROTEIN MUTEINS

[75] Inventors: Georgia Theofan, Torrance; Arnold Horwitz, Los Angeles; David Burke, Oakland; Manik Baltaian, Glendale, all of Calif.; Lynn Grinna, Middleburg, Va.

[73] Assignee: Xoma Corporation, Berkeley, Calif.

[21] Appl. No.: 13,801

[22] Filed: Feb. 2, 1993

[51] Int. Cl.$^6$ ............ C12P 21/06; C12N 15/00; C07K 14/435
[52] U.S. Cl. ............ 435/69.1; 530/350; 536/23.5; 435/320.1; 435/252.3
[58] Field of Search ............ 530/350; 536/23.5; 435/320.1, 252.3, 69.1

[56] References Cited

U.S. PATENT DOCUMENTS

| | | | |
|---|---|---|---|
| Re. 33,653 | 7/1991 | Mark et al. | 424/85.1 |
| 4,518,584 | 5/1985 | Mark et al. | 424/85.1 |
| 4,588,585 | 5/1986 | Mark et al. | 424/85.1 |
| 4,677,063 | 6/1987 | Mark et al. | 435/68.1 |
| 4,677,064 | 6/1987 | Mark et al. | 435/68.1 |
| 4,816,566 | 3/1989 | DeChiara et al. | 530/351 |
| 4,853,332 | 8/1989 | Mark et al. | 435/252.33 |
| 4,879,226 | 11/1989 | Wallace et al. | 435/68.1 |
| 4,959,314 | 9/1990 | Mark et al. | 435/69.1 |
| 5,089,274 | 2/1992 | Marra et al. | 424/534 |
| 5,171,739 | 2/1992 | Scott | 514/12 |
| 5,198,541 | 3/1993 | Elsbach et al. | 435/69.1 |
| 5,206,344 | 4/1993 | Katre et al. | 530/351 |
| 5,234,912 | 8/1993 | Marra et al. | 514/21 |
| 5,308,834 | 5/1994 | Scott et al. | 514/12 |
| 5,334,584 | 8/1994 | Scott et al. | 514/12 |
| 5,348,942 | 9/1994 | Little, II et al. | 514/12 |

FOREIGN PATENT DOCUMENTS

| | | |
|---|---|---|
| WO89/01486 | 2/1989 | WIPO . |
| WO90/12874 | 11/1990 | WIPO . |
| WO92/03535 | 3/1992 | WIPO . |
| WO92/09621 | 6/1992 | WIPO . |
| WO93/05797 | 4/1993 | WIPO . |
| WO93/06228 | 4/1993 | WIPO . |
| WO93/23434 | 11/1993 | WIPO . |
| WO93/23540 | 11/1993 | WIPO . |
| WO94/17819 | 8/1994 | WIPO . |
| WO94/18323 | 8/1994 | WIPO . |
| WO94/20128 | 9/1994 | WIPO . |
| WO94/20129 | 9/1994 | WIPO . |

OTHER PUBLICATIONS

Bebbington et al., "High-Level Expression of a Recombinant Antibody from Myeloma Cells Using a Glutamine Synthetase Gene as an Amplifiable Selectable Marker", *Bio/Technology*, 10(2):169–175 (Feb. 1992).

Boshart et al., "A Very Strong Enhancer is Located Upstream of an Immediate Early Gene of Human Cytomegalovirus", *Cell* 41:521–530 (Jun. 1985).

Elsbach et al., "Separation and Purification of a Potent Bactericidal/Permeability-increasing Protein and a Closely Associated Phospholipase $A_2$ from Rabbit Polymorphonuclear Leukocytes", *J. Biol. Chem.*, 254(21):11000–11009 (Nov. 10, 1979).

Gazzano-Santoro et al., "High-Affinity Binding of the Bactericidal/Permeability-Increasing Protein and a Recombinant Amino-Terminal Fragment to the Lipid A Region of Lipopolysaccharide", *Infect. Immun.* 60(11):4754–4761 (Nov. 1992).

(List continued on next page.)

*Primary Examiner*—Robert A. Wax
*Assistant Examiner*—Keith D. Hendricks
*Attorney, Agent, or Firm*—Marshall, O'Toole, Gerstein, Murray & Borun

[57] ABSTRACT

Disclosed are novel bactericidal/permeability-increasing (BPI) protein products wherein cysteine residue number 132 or 135 is replaced by another amino acid residue, preferably an alanine or serine residue and/or wherein the leucine residue at position 193 is the carboxy terminal residue. Also disclosed are DNA sequences encoding methods for the production of the same in appropriate host cells, and stable homogeneous pharmaceutical compositions containing the analogs suitable for use treatment of gram negative bacterial infection and its sequelae.

19 Claims, 8 Drawing Sheets

OTHER PUBLICATIONS

Gray et al., "Cloning of the cDNA of a Human Neutrophil Bactericidal Protein", *J. Biol. Chem.*, 264(16):9505-9509 (Jun. 5, 1989).

Habuka et al., "Substantial Increase of the Inhibitory Activity of Mirabilis Antiviral Protein by an Elimination of the Disulfide Bond with Genetic Engineering", *J. Biol. Chem.*, 266(35):23558-23560 (Dec. 15, 1991).

Hartman and Mulligan, "Two dominant-acting selectable markers for gene transfer studies in mammalian cells", *Proc. Nat. Acad. Sci. USA*, 85:8047-8051 (Nov. 1988).

Kaback, "Use of Site-Directed Mutagenesis to Study the Mechanism of a Membrane Transport Protein", *Biochemistry*, 26(8):2071-2076 (Apr. 21, 1987).

Kozak, "An analysis of 5'-noncoding sequences from 699 vertebrate messenger RNAs", *Nucl. Acid. Res.*, 15(20):8125-8148 (1987).

Lambert et al., "Recombinant Bactericidal/Permeability-Increasing (rBPI) Protein Kills both Gram-Positive and Gram-Negative Bacteria", *Abstracts of the 34th Interscience Conference on Antimicrobial Agents and Chemotherapy*, Abstract #C/6 (Oct. 4-7 1994).

Liang et al., "Studies of Structure-Activity Relationships of Human Interleukin-2", *J. Biol. Chem.*, 261(1):334-337 (Jan. 5, 1986).

Lui et al., "Production of a Mouse-Human Chimeric Monoclonal Antibody to CD20 with Potent Fc-Dependent Biologic Activity", *J. Immunol.*, 139(10):3521-3526 (Nov. 15, 1987).

Mark et al., "Site-specific mutagenesis of the human fibroblast interferon gene", *Proc. Natl. Acad. Sci. USA*, 81:0000-0000 (Sep. 1984).

Morrison, "The case for specific lipopolysaccharide receptors expressed on mammalian cells", *Microb. Pathogenesis*, 7:389-398 (1989).

Morrison and Ryan, "Endotoxins and Disease Mechanisms", *Ann. Rev. Med.*, 38:417-432 (1987).

Mulligan and Berg, "Selection for animal cells that express the *Escherichia coli* gene coding for xanthine-guanine phosphoribosyltransferase", *Proc. Nat. Acad. Sci. USA*, 78(4):2072-2076 (Apr. 1981).

Ooi et al., "Endotoxin-neutralizing Properties of the 25 kD N-Terminal Fragment and a Newly Isolated 30 kD C-Terminal Fragment of the 55-60 kD Bactericidal/Permeability-increasing Protein of Human Neutrophils", *J. Exp. Med.*, 174:649-655 (Sep. 1991).

Perry and Wetzel, "unpaired Cysteine-54 Interferes with the Ability of an Engineered Disulfide to Stabilize T4 Lysozyme", *Biochemistry*, 25(3):733-739 (1986).

Raetz, "Biochemistry of Endotoxins", *Ann. Rev. Biochem.*, 59:129-170 (1990).

Rastetter, "Enzyme engineering: applications and Promise", *Trends Biotech.* 1(3) (1983).

Roeder et al., "Endotoxic-Lipopolysaccharide-Specific Binding Proteins on Lymphoid Cells of Various Animal Species: Association with Endotoxin Susceptibility", *Infect., Immun.*, 57(4):1054-1058 (Apr. 1989).

Rusk et al., "Structure-Function Relationships for the IL-2 Receptor System", *J. Immunol.*, 140(7):2249-2259 (Apr. 1, 1988).

Sambrook et al., "Introduction of Recombinant Vectors into Mammalian Cells", in *Molecular Cloning: A Laboratory Manual*, pp. 16.30-16.31 (1989).

Shepard et al., "A single amino acid change in IFN-$\beta_1$ abolishes its antiviral activity", Nature, 294:563-565 (Dec. 10, 1981).

Simon and Praag, "Inhibition of RNA Synthesis in *Escherichia coli* by Levorphanol", *Proc. N. A. S.*, 51:877-883 (1964).

Snouwaert et al., "Effects of Site-Specific Mutations on Biologic Activities of Recombinant Human IL-2", *J. Immunol.*, 146(2):585-591 (Jan. 15, 1991).

Snouwaert et al., "Role of Disulfide Bonds in Biologic Activity of Human Interleukin-6", *J. Biol. Chem.*, 266(34):23097-23102 (Dec. 5, 1991).

Southern and Berg, "Transformation of Mammalian Cells to Antibiotic Resistance with a Bacterial Gene Under Control of the SV40 Early Region Promoter", *J. Mol. Appl. Genet.*, 1:327-341 (1982).

OTHER PUBLICATIONS

Velan et al., "The Effect of Elimination of Intersubunit Disulfide Bonds on the Activity, Assembly, and Secretion of Recombinant Human Acetylcholinesterase", *J. Biol. Chem.*, 266(35):23977–23984 (Dec. 15, 1991).

Wang et al., Site -Specific Mutagenesis of the Human Interleukin-2 Gene: Structure-Function Analysis of the Cysteine Residues, *Science*, 244:1431–1433 (Jun. 29, 1984).

Weiss and Olsson, "Cellular and Subcellular Localization of the Bactericidal/Permeability–Increasing Protein of Neutrophils", *Blood*, 69(2):652–659 (Feb. 1987).

Wetzel, "Harnessing disulfide bonds using protein engineering", *TIBS.*, 12:478–482 (Dec. 1987).

Wilkinson et al., "Site-Directed Mutagenesis as a Probe of Enzyme Structure and Catalysis: Tyrosyl-tRNA Synthetase Cysteine-35 to Glycine-35 Mutation", *Biochemistry*, 22(15):3586–3594 (1983).

Winter et al., "Redesigning enzyme structure by site-directed mutagenesis:tyrosyl tRNA synthesis and ATP binding", *Nature*, 299:756–758 (Oct. 21, 1982).

Xu et al., "Transcription Termination and Chromatin Structure of the Active Immunoglobulin $\kappa$ Gene Locus", *J. Biol. Chem.*, 261(8):3838–3845 (Mar. 15, 1986).

Zoller and Smith, "Oligonucleotide-Directed Mutagenesis of DNA Fragments Cloned into M13 Vectors", *Meth. Enzymol.*, 100:468–500 (1983).

Legend:
1 = Novex Standards
2 = rBPI$_{23}$ lot R53-R73/NB2255m 2.6 ug.
3 = C132A, 1 ug
4 = C132A, 2 ug
5 = C132A, 4 ug
6 = C132A, 6 ug
7 = rBPI$_{23}$ sample BR-1, 1.8 ug
8 = rBPI$_{23}$ sample BR-1, 3.7 ug
9 = rBPI$_{23}$ sample BR-1, 6.4 ug
10 = rBPI$_{23}$ sample BR-1, 9.2 ug Legend:
1 = Novex Standards
2 = rBPI$_{23}$ lot R53-R73/NB2255
3 = rBPI$_{23}$ lot BR-1
4 = C132A, lot B166
1-4 Non-reduced
7 = C132A lot B166
8 = rBPI$_{23}$ lot BR-1
9 = rBPI$_{23}$ lot R53-R73/NB2255
10 = Novex Standards
7-9 Reduced

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
      ( A ) LENGTH: 1813 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
      ( A ) NAME/KEY: CDS
      ( B ) LOCATION: 31..1491

( i x ) FEATURE:
      ( A ) NAME/KEY: matpeptide
      ( B ) LOCATION: 124..1491

( x i ) SEQUENCE DESCRIPTION: SEQ ID NO:1:

```
CAGGCCTTGA GGTTTTGGCA GCTCTGGAGG ATG AGA GAG AAC ATG GCC AGG GGC    54
                                  Met Arg Glu Asn Met Ala Arg Gly
                                  -31 -30                     -25

CCT TGC AAC GCG CCG AGA TGG GTG TCC CTG ATG GTG CTC GTC GCC ATA   102
Pro Cys Asn Ala Pro Arg Trp Val Ser Leu Met Val Leu Val Ala Ile
            -20             -15                     -10

GGC ACC GCC GTG ACA GCG GCC GTC AAC CCT GGC GTC GTG GTC AGG ATC   150
Gly Thr Ala Val Thr Ala Ala Val Asn Pro Gly Val Val Val Arg Ile
         -5               1                5

TCC CAG AAG GGC CTG GAC TAC GCC AGC CAG CAG GGG ACG GCC GCT CTG   198
Ser Gln Lys Gly Leu Asp Tyr Ala Ser Gln Gln Gly Thr Ala Ala Leu
 10              15                  20                      25

CAG AAG GAG CTG AAG AGG ATC AAG ATT CCT GAC TAC TCA GAC AGC TTT   246
Gln Lys Glu Leu Lys Arg Ile Lys Ile Pro Asp Tyr Ser Asp Ser Phe
                 30                  35                  40

AAG ATC AAG CAT CTT GGG AAG GGG CAT TAT AGC TTC TAC AGC ATG GAC   294
Lys Ile Lys His Leu Gly Lys Gly His Tyr Ser Phe Tyr Ser Met Asp
             45                  50                  55

ATC CGT GAA TTC CAG CTT CCC AGT TCC CAG ATA AGC ATG GTG CCC AAT   342
Ile Arg Glu Phe Gln Leu Pro Ser Ser Gln Ile Ser Met Val Pro Asn
         60                  65                  70

GTG GGC CTT AAG TTC TCC ATC AGC AAC GCC AAT ATC AAG ATC AGC GGG   390
Val Gly Leu Lys Phe Ser Ile Ser Asn Ala Asn Ile Lys Ile Ser Gly
     75                  80                  85

AAA TGG AAG GCA CAA AAG AGA TTC TTA AAA ATG AGC GGC AAT TTT GAC   438
Lys Trp Lys Ala Gln Lys Arg Phe Leu Lys Met Ser Gly Asn Phe Asp
 90                  95                 100                 105

CTG AGC ATA GAA GGC ATG TCC ATT TCG GCT GAT CTG AAG CTG GGC AGT   486
Leu Ser Ile Glu Gly Met Ser Ile Ser Ala Asp Leu Lys Leu Gly Ser
                 110                 115                 120

AAC CCC ACG TCA GGC AAG CCC ACC ATC ACC TGC TCC AGC TGC AGC AGC   534
Asn Pro Thr Ser Gly Lys Pro Thr Ile Thr Cys Ser Ser Cys Ser Ser
             125                 130                 135

CAC ATC AAC AGT GTC CAC GTG CAC ATC TCA AAG AGC AAA GTC GGG TGG   582
His Ile Asn Ser Val His Val His Ile Ser Lys Ser Lys Val Gly Trp
         140                 145                 150

CTG ATC CAA CTC TTC CAC AAA AAA ATT GAG TCT GCG CTT CGA AAC AAG   630
Leu Ile Gln Leu Phe His Lys Lys Ile Glu Ser Ala Leu Arg Asn Lys
     155                 160                 165

ATG AAC AGC CAG GTC TGC GAG AAA GTG ACC AAT TCT GTA TCC TCC AAG   678
Met Asn Ser Gln Val Cys Glu Lys Val Thr Asn Ser Val Ser Ser Lys
170                 175                 180                 185

CTG CAA CCT TAT TTC CAG ACT CTG CCA GTA ATG ACC AAA ATA GAT TCT   726
Leu Gln Pro Tyr Phe Gln Thr Leu Pro Val Met Thr Lys Ile Asp Ser
                190                 195                 200

GTG GCT GGA ATC AAC TAT GGT CTG GTG GCA CCT CCA GCA ACC ACG GCT   774
Val Ala Gly Ile Asn Tyr Gly Leu Val Ala Pro Pro Ala Thr Thr Ala
            205                 210                 215

GAG ACC CTG GAT GTA CAG ATG AAG GGG GAG TTT TAC AGT GAG AAC CAC   822
Glu Thr Leu Asp Val Gln Met Lys Gly Glu Phe Tyr Ser Glu Asn His
        220                 225                 230

CAC AAT CCA CCT CCC TTT GCT CCA CCA GTG ATG GAG TTT CCC GCT GCC   870
His Asn Pro Pro Pro Phe Ala Pro Pro Val Met Glu Phe Pro Ala Ala
    235                 240                 245

CAT GAC CGC ATG GTA TAC CTG GGC CTC TCA GAC TAC TTC TTC AAC ACA   918
His Asp Arg Met Val Tyr Leu Gly Leu Ser Asp Tyr Phe Phe Asn Thr
250                 255                 260                 265

GCC GGG CTT GTA TAC CAA GAG GCT GGG GTC TTG AAG ATG ACC CTT AGA   966
Ala Gly Leu Val Tyr Gln Glu Ala Gly Val Leu Lys Met Thr Leu Arg
                270                 275                 280
```

| | | | | | | | | | | | | | | | |
|---|---|---|---|---|---|---|---|---|---|---|---|---|---|---|---|
| GAT | GAC | ATG | ATT | CCA | AAG | GAG | TCC | AAA | TTT | CGA | CTG | ACA | ACC | AAG | TTC | 1014 |
| Asp | Asp | Met | Ile 285 | Pro | Lys | Glu | Ser 290 | Lys | Phe | Arg | Leu | Thr 295 | Thr | Lys | Phe | |
| TTT | GGA | ACC | TTC | CTA | CCT | GAG | GTG | GCC | AAG | AAG | TTT | CCC | AAC | ATG | AAG | 1062 |
| Phe | Gly | Thr 300 | Phe | Leu | Pro | Glu | Val 305 | Ala | Lys | Lys | Phe | Pro 310 | Asn | Met | Lys | |
| ATA | CAG | ATC | CAT | GTC | TCA | GCC | TCC | ACC | CCG | CCA | CAC | CTG | TCT | GTG | CAG | 1110 |
| Ile | Gln | Ile 315 | His | Val | Ser | Ala | Ser 320 | Thr | Pro | Pro | His 325 | Leu | Ser | Val | Gln | |
| CCC | ACC | GGC | CTT | ACC | TTC | TAC | CCT | GCC | GTG | GAT | GTC | CAG | GCC | TTT | GCC | 1158 |
| Pro 330 | Thr | Gly | Leu | Thr | Phe 335 | Tyr | Pro | Ala | Val | Asp 340 | Val | Gln | Ala | Phe | Ala 345 | |
| GTC | CTC | CCC | AAC | TCC | TCC | CTG | GCT | TCC | CTC | TTC | CTG | ATT | GGC | ATG | CAC | 1206 |
| Val | Leu | Pro | Asn 350 | Ser | Ser | Leu | Ala | Ser 355 | Leu | Phe | Leu | Ile | Gly 360 | Met | His | |
| ACA | ACT | GGT | TCC | ATG | GAG | GTC | AGC | GCC | GAG | TCC | AAC | AGG | CTT | GTT | GGA | 1254 |
| Thr | Thr | Gly | Ser 365 | Met | Glu | Val | Ser | Ala 370 | Glu | Ser | Asn | Arg | Leu 375 | Val | Gly | |
| GAG | CTC | AAG | CTG | GAT | AGG | CTG | CTC | CTG | GAA | CTG | AAG | CAC | TCA | AAT | ATT | 1302 |
| Glu | Leu | Lys 380 | Leu | Asp | Arg | Leu | Leu 385 | Leu | Glu | Leu | Lys | His 390 | Ser | Asn | Ile | |
| GGC | CCC | TTC | CCG | GTT | GAA | TTG | CTG | CAG | GAT | ATC | ATG | AAC | TAC | ATT | GTA | 1350 |
| Gly | Pro 395 | Phe | Pro | Val | Glu | Leu 400 | Leu | Gln | Asp | Ile | Met 405 | Asn | Tyr | Ile | Val | |
| CCC | ATT | CTT | GTG | CTG | CCC | AGG | GTT | AAC | GAG | AAA | CTA | CAG | AAA | GGC | TTC | 1398 |
| Pro 410 | Ile | Leu | Val | Leu | Pro 415 | Arg | Val | Asn | Glu | Lys 420 | Leu | Gln | Lys | Gly | Phe 425 | |
| CCT | CTC | CCG | ACG | CCG | GCC | AGA | GTC | CAG | CTC | TAC | AAC | GTA | GTG | CTT | CAG | 1446 |
| Pro | Leu | Pro | Thr | Pro 430 | Ala | Arg | Val | Gln | Leu 435 | Tyr | Asn | Val | Val | Leu 440 | Gln | |
| CCT | CAC | CAG | AAC | TTC | CTG | CTG | TTC | GGT | GCA | GAC | GTT | GTC | TAT | AAA | | 1491 |
| Pro | His | Gln | Asn 445 | Phe | Leu | Leu | Phe | Gly 450 | Ala | Asp | Val | Val | Tyr 455 | Lys | | |

```
TGAAGGCACC AGGGGTGCCG GGGGCTGTCA GCCGCACCTG TTCCTGATGG GCTGTGGGGC  1551
ACCGGCTGCC TTTCCCCAGG GAATCCTCTC CAGATCTTAA CCAAGAGCCC CTTGCAAACT  1611
TCTTCGACTC AGATTCAGAA ATGATCTAAA CACGAGGAAA CATTATTCAT TGGAAAAGTG  1671
CATGGTGTGT ATTTTAGGGA TTATGAGCTT CTTTCAAGGG CTAAGGCTGC AGAGATATTT  1731
CCTCCAGGAA TCGTGTTTCA ATTGTAACCA AGAAATTTCC ATTTGTGCTT CATGAAAAAA  1791
AACTTCTGGT TTTTTTCATG TG                                          1813
```

( 2 ) INFORMATION FOR SEQ ID NO:2:

( i ) SEQUENCE CHARACTERISTICS:
        ( A ) LENGTH: 487 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met -31 | Arg -30 | Glu | Asn | Met | Ala -25 | Arg | Gly | Pro | Cys | Asn -20 | Ala | Pro | Arg | Trp | Val |
| Ser -15 | Leu | Met | Val | Leu | Val -10 | Ala | Ile | Gly | Thr | Ala -5 | Val | Thr | Ala | Ala | Val 1 |
| Asn | Pro | Gly | Val 5 | Val | Val | Arg | Ile | Ser 10 | Gln | Lys | Gly | Leu | Asp 15 | Tyr | Ala |
| Ser | Gln | Gln | Gly 20 | Thr | Ala | Ala | Leu | Gln 25 | Lys | Glu | Leu | Lys | Arg 30 | Ile | Lys |
| Ile | Pro | Asp | Tyr | Ser | Asp | Ser | Phe | Lys | Ile | Lys | His | Leu | Gly | Lys | Gly |

| | 35 | | | | 40 | | | | | 45 | | | |
|---|---|---|---|---|---|---|---|---|---|---|---|---|---|
| His | Tyr | Ser | Phe | Tyr | Ser | Met | Asp | Ile | Arg | Glu | Phe | Gln | Leu | Pro | Ser |
| 50 | | | | | 55 | | | | | 60 | | | | | 65 |
| Ser | Gln | Ile | Ser | Met | Val | Pro | Asn | Val | Gly | Leu | Lys | Phe | Ser | Ile | Ser |
| | | | | 70 | | | | | 75 | | | | | 80 | |
| Asn | Ala | Asn | Ile | Lys | Ile | Ser | Gly | Lys | Trp | Lys | Ala | Gln | Lys | Arg | Phe |
| | | | 85 | | | | | 90 | | | | | 95 | | |
| Leu | Lys | Met | Ser | Gly | Asn | Phe | Asp | Leu | Ser | Ile | Glu | Gly | Met | Ser | Ile |
| | | 100 | | | | | 105 | | | | | 110 | | | |
| Ser | Ala | Asp | Leu | Lys | Leu | Gly | Ser | Asn | Pro | Thr | Ser | Gly | Lys | Pro | Thr |
| | 115 | | | | | 120 | | | | | 125 | | | | |
| Ile | Thr | Cys | Ser | Ser | Cys | Ser | Ser | His | Ile | Asn | Ser | Val | His | Val | His |
| 130 | | | | | 135 | | | | | 140 | | | | | 145 |
| Ile | Ser | Lys | Ser | Lys | Val | Gly | Trp | Leu | Ile | Gln | Leu | Phe | His | Lys | Lys |
| | | | | 150 | | | | | 155 | | | | | 160 | |
| Ile | Glu | Ser | Ala | Leu | Arg | Asn | Lys | Met | Asn | Ser | Gln | Val | Cys | Glu | Lys |
| | | | 165 | | | | | 170 | | | | | 175 | | |
| Val | Thr | Asn | Ser | Val | Ser | Ser | Lys | Leu | Gln | Pro | Tyr | Phe | Gln | Thr | Leu |
| | | 180 | | | | | 185 | | | | | 190 | | | |
| Pro | Val | Met | Thr | Lys | Ile | Asp | Ser | Val | Ala | Gly | Ile | Asn | Tyr | Gly | Leu |
| | 195 | | | | | 200 | | | | | 205 | | | | |
| Val | Ala | Pro | Pro | Ala | Thr | Thr | Ala | Glu | Thr | Leu | Asp | Val | Gln | Met | Lys |
| 210 | | | | | 215 | | | | | 220 | | | | | 225 |
| Gly | Glu | Phe | Tyr | Ser | Glu | Asn | His | His | Asn | Pro | Pro | Pro | Phe | Ala | Pro |
| | | | | 230 | | | | | 235 | | | | | 240 | |
| Pro | Val | Met | Glu | Phe | Pro | Ala | Ala | His | Asp | Arg | Met | Val | Tyr | Leu | Gly |
| | | | 245 | | | | | 250 | | | | | 255 | | |
| Leu | Ser | Asp | Tyr | Phe | Phe | Asn | Thr | Ala | Gly | Leu | Val | Tyr | Gln | Glu | Ala |
| | | 260 | | | | | 265 | | | | | 270 | | | |
| Gly | Val | Leu | Lys | Met | Thr | Leu | Arg | Asp | Asp | Met | Ile | Pro | Lys | Glu | Ser |
| | 275 | | | | | 280 | | | | | 285 | | | | |
| Lys | Phe | Arg | Leu | Thr | Thr | Lys | Phe | Phe | Gly | Thr | Phe | Leu | Pro | Glu | Val |
| 290 | | | | | 295 | | | | | 300 | | | | | 305 |
| Ala | Lys | Lys | Phe | Pro | Asn | Met | Lys | Ile | Gln | Ile | His | Val | Ser | Ala | Ser |
| | | | | 310 | | | | | 315 | | | | | 320 | |
| Thr | Pro | Pro | His | Leu | Ser | Val | Gln | Pro | Thr | Gly | Leu | Thr | Phe | Tyr | Pro |
| | | | 325 | | | | | 330 | | | | | 335 | | |
| Ala | Val | Asp | Val | Gln | Ala | Phe | Ala | Val | Leu | Pro | Asn | Ser | Ser | Leu | Ala |
| | | 340 | | | | | 345 | | | | | 350 | | | |
| Ser | Leu | Phe | Leu | Ile | Gly | Met | His | Thr | Thr | Gly | Ser | Met | Glu | Val | Ser |
| | 355 | | | | | 360 | | | | | 365 | | | | |
| Ala | Glu | Ser | Asn | Arg | Leu | Val | Gly | Glu | Leu | Lys | Leu | Asp | Arg | Leu | Leu |
| 370 | | | | | 375 | | | | | 380 | | | | | 385 |
| Leu | Glu | Leu | Lys | His | Ser | Asn | Ile | Gly | Pro | Phe | Pro | Val | Glu | Leu | Leu |
| | | | | 390 | | | | | 395 | | | | | 400 | |
| Gln | Asp | Ile | Met | Asn | Tyr | Ile | Val | Pro | Ile | Leu | Val | Leu | Pro | Arg | Val |
| | | | 405 | | | | | 410 | | | | | 415 | | |
| Asn | Glu | Lys | Leu | Gln | Lys | Gly | Phe | Pro | Leu | Pro | Thr | Pro | Ala | Arg | Val |
| | | 420 | | | | | 425 | | | | | 430 | | | |
| Gln | Leu | Tyr | Asn | Val | Val | Leu | Gln | Pro | His | Gln | Asn | Phe | Leu | Leu | Phe |
| | 435 | | | | | 440 | | | | | 445 | | | | |
| Gly | Ala | Asp | Val | Val | Tyr | Lys | | | | | | | | | |
| 450 | | | | | 455 | | | | | | | | | | |

( 2 ) INFORMATION FOR SEQ ID NO:3:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:3:

AAGCTTGTCG ACCAGGCCTT GAGGT  25

( 2 ) INFORMATION FOR SEQ ID NO:4:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:4:

CTGGAGGCGG TGATGGTG  18

( 2 ) INFORMATION FOR SEQ ID NO:5:

( i ) SEQUENCE CHARACTERISTICS:
  ( A ) LENGTH: 19 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:5:

CTCCAGCAGC CACATCAAC  19

( 2 ) INFORMATION FOR SEQ ID NO:6:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:6:

GAACTTGGTT GTCAGTCG  18

( 2 ) INFORMATION FOR SEQ ID NO:7:

( i ) SEQUENCE CHARACTERISTICS:
  ( A ) LENGTH: 13 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO:7:

GCCACCRCCA TGG  13

( 2 ) INFORMATION FOR SEQ ID NO:8:

( i ) SEQUENCE CHARACTERISTICS:
  ( A ) LENGTH: 27 base pairs
  ( B ) TYPE: nucleic acid
  ( C ) STRANDEDNESS: single
  ( D ) TOPOLOGY: linear (i i) MOLECULE TYPE: cDNA (x i) SEQUENCE DESCRIPTION: SEQ ID NO:8:

ACTGTCGACG CCACCATGGC CAGGGGC 27

(2) INFORMATION FOR SEQ ID NO:9:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:9:

CCGCGGCTCG AGCTATATTT TGGTCAT 27

(2) INFORMATION FOR SEQ ID NO:10:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:10:

CTGTAGCTCG AGCCGC 16

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:11:

GGCTCGAGCT ACAGAGT 17

(2) INFORMATION FOR SEQ ID NO:12:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:12:

GTCGACGCAT GCGAGAGAAC ATGGC 25

(2) INFORMATION FOR SEQ ID NO:13:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:13:

GACGCCACCA TGGTC 15

( 2 ) INFORMATION FOR SEQ ID NO:14:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:14:

GACCATGGTG GCGTC                                          15

STABLE BACTERICIDAL/PERMEABILITY-INCREASING PROTEIN MUTEINS

BACKGROUND OF THE INVENTION

The present invention provides novel bactericidal/-permeability-increasing protein products and stable pharmaceutical compositions containing the same.

Lipopolysaccharide (LPS), is a major component of the outer membrane of gram-negative bacteria and consists of serotype-specific O-side-chain polysaccharides linked to a conserved region of core oligosaccharide and lipid A. Raetz, *Ann. Rev. Biochem.*, 59:129-170 (1990). LPS is an important mediator in the pathogenesis of gram-negative septic shock, one of the major causes of death in intensive-care units in the United States. Morrison, et al., *Ann. Rev. Med.* 38:417-432 (1987).

LPS-binding proteins have been identified in various mammalian tissues. Morrison, *Microb. Pathol.*, 7:389-398 (1989); Roeder, et al., *Infect., Immun.*, 57:1054-1058 (1989). Among the most extensively studied of the LPS-binding proteins is bactericidal/permeability-increasing protein (BPI), a basic protein found in the azurophilic granules of polymorphonuclear leukocytes. Human BPI protein has been isolated from polymorphonuclear neutrophils by acid extraction combined with either ion exchange chromatography [Elsbach, *J. Biol. Chem.*, 254:11000 (1979)] or *E. coli* affinity chromatography [Weiss, et al., *Blood,* 69:652 (1987)] and has potent bactericidal activity against a broad spectrum of gram-negative bacteria.

While the BPI protein is cytotoxic against many gram-negative bacteria, it has no reported cytotoxic activity toward gram-positive bacteria, fungi, or mammalian cells. The amino acid sequence of the entire human BPI protein, as well as the DNA encoding the protein, have been elucidated in FIG. 1 of Gray, et al., *J. Biol. Chem.*, 264:9505 (1989), incorporated herein by reference (SEQ ID NOs: 1 and 2). The Gray et al. publication discloses the isolation of human BPI-encoding cDNA from a cDNA library derived from DMSO-induced cells of the human promyelocytic leukemia HL-60 cell line (ATTC CCL 240). Multiple PCR amplifications of DNA from a freshly prepared cDNA library derived from such DMSO-induced HL-60 cells have revealed the existence of human BPI-encoding cDNAs wherein the codon specifying valine at amino acid position 151 is either GTC (as set out in SEQ ID No: 1) or GTG. Moreover, cDNA species employing GTG to specify valine at position 151 have also been found to specify either lysine (AAG) for the position 185 amino acid (as in SEQ ID Nos: 1 and 2) or a glutamic acid residue (GAG) at that position.

A proteolytic fragment corresponding to the N-terminal portion of human BPI holoprotein possesses the antibacterial efficacy of the naturally-derived 55 kDa human BPI holoprotein. In contrast to the N-terminal portion, the C-terminal region of the isolated human BPI protein displays only slightly detectable anti-bacterial activity. Ooi, et al., *J. Exp. Med.*, 174:649 (1991). A BPI N-terminal fragment, comprising approximately the first 199 amino acids of the human BPI holoprotein, has been produced by recombinant means as a 23 kD protein. Gazzano-Santoro et al., *Infect. Immun.* 60:4754-4761 (1992).

The projected clinical use of BPI products for treatment of gram-negative sepsis in humans has prompted significant efforts to produce large quantities of recombinant BPI (rBPI) products suitable for incorporation into stable, homogeneous pharmaceutical preparations. For example, co-owned, co-pending U.S. patent application Ser. No. 07/885,501 by Grinna discloses novel methods for the purification of recombinant BPI products expressed in and secreted from genetically transformed mammalian host cells in culture. Efficacy of the purification processes is therein demonstrated in the context of products of transformed CHO cells which express DNA encoding the 31 amino acid "leader" sequence of human BPI and the initial 199 amino terminal residues of the mature protein (i.e. corresponding to the amino acids −31 through 199 of SEQ ID NO: 2). Co-owned, co-pending U.S. patent application Ser. No. 07/885,911 by Theofan, et al. is directed to novel, recombinant-produced BPI protein analog products resulting from the expression of DNA encoding the BPI leader sequence and either 191 or 199 amino terminal residues of human BPI fused to DNA encoding a constant region of an immunoglobulin heavy chain.

Efforts to produce pharmaceutical grade BPI products for treatment of gram negative sepsis in humans have not yielded uniformly satisfactory results. A principal reason for this is the nature of the amino acid sequence of human BPI and the nature of the recombinant host cell environment in which the products are produced. As one example, biologically-active rBPI products comprising the initial 199 residues of BPI [rBPI(1-199)] produced as secretory products of transfected CHO host cells may be purified in good yields. However, the isolated BPI products initially include dimeric forms of BPI as well as cysteine adduct species. Moreover, BPI products may be unstable upon storage at physiological temperature and pH, resulting in the formation of additional dimeric and adduct species. Such dimeric and adduct species, while retaining biological activity, are not preferred for incorporation into pharmaceutical preparations projected for human use. Dimer formation and the formation of cysteine adducts are the probable result of the fact that BPI includes three cysteine amino acid residues, all of which are positioned within the biologically active amino terminal region of BPI, i.e., at positions 132, 135 and 175. Formation of a single disulfide bond between two of the three cysteines allows for dimer formation or formation of cysteine adducts with the remaining free cysteine in the host cell cytoplasm and/or the cell culture supernatant.

Even monomeric rBPI products display varying degrees of microheterogeneity in terms of the number of carboxy terminal residues present in such products. For example, it is difficult to detect full-length expression product in a medium containing host cells transformed or transfected with DNA encoding rBPI(1-199). Instead, the expression products obtained from such cells represent an heterogeneous array of carboxy-terminal truncated species of the rBPI N-terminal fragment. In fact, the expected full-length product (1-199) is often not detected as being among the rBPI species present in that heterogeneous array. Heterogeneity of the carboxy terminal amino acid sequence of rBPI(1-199) products appears to result from activity of carboxypeptidases in host cell cytoplasm and/or culture supernatant.

An additional problem encountered in the preparation of pharmaceutical-grade BPI products is the formation of macroscopic particles which decrease the homogeneity of the product, as well as decreasing its activity. A preferred pharmaceutical composition containing rBPI products according to the invention comprises the combination of a poloxamer (polyoxypropylenepolyoxyethylene block copolymer) surfactant and a polysorbate (polyoxyethylene sorbitan fatty acid ester) surfactant. Such combinations are taught in co-owned, co-pending, concurrently-filed U.S. patent application Ser. No. 08/012,360, now abandoned, to have synergistic effects in stabilizing pharmaceutically-active polypeptides against particle formation. Most preferred is a composition in which the rBPI product is present in a concentration of 1 mg/ml in citrate buffered saline (0.02M citrate, 0.15M NaCl, pH 5.0) comprising 0.1% by weight of poloxamer 188 (Pluronic F-68, BASF Wyandotte, Parsippany, N.J.) and 0.002% by weight of polysorbate 80 (Tween 80, ICI Americas Inc., Wilmington, Del.).

There continues to be a need in the art for improved rBPI products suitable for incorporation into stable homogeneous pharmaceutical preparations. Such products would ideally be obtainable in large yield from transformed host cells, would retain the bactericidal and LPS-binding biological activities of BPI, and would be limited in their capacity to form dimeric species and Cysteine adducts, and would be characterized by limited variation in carboxy termini.

SUMMARY OF THE INVENTION

The present invention provides novel, biologically-active, recombinant-produced BPI ("rBPI") protein and protein fragment products which are characterized by a resistance to dimerization and cysteine adduct formation, making such products highly suitable for pharmaceutical use. Also provided are rBPI products characterized by decreased molecular heterogeneity at the carboxy terminus. Novel DNA sequences encoding rBPI products and analog products, plasmid vectors containing the DNA, host cells stably transformed or transfected with the plasmids, recombinant preparative methods, stable pharmaceutical compositions and treatment methods are also provided by the invention.

According to one aspect of the present invention, rBPI protein analogs are provided which comprise a BPI N-terminal fragment wherein a cysteine at amino acid position 132 or 135 is replaced by another amino acid, preferably a non-polar amino acid such as serine or alanine. In a preferred embodiment of the invention, the cysteine residue at position 132 of a polypeptide comprising the first 199 N-terminal residues of BPI is replaced by an alanine residue in a recombinant product designated "rBPI(1-199)ala$^{132}$". Also in a preferred embodiment of the invention, the cysteine at position 135 of a BPI fragment comprising the first 199 N-terminal BPI residues is replaced by a serine, resulting in a recombinant product designated "rBPI(1-199)ser$^{135}$". Highly preferred is a recombinant product designated "rBPI(1-193)ala$^{132}$" which is characterized by decreased heterogeneity in terms of the identity of its carboxy terminal residue. Also in a preferred embodiment of the invention, a polypeptide is taught which comprises the first 193 amino-terminal residues of BPI and which has a stop codon immediately following the codon for leucine at position 193.

According to another aspect of the invention, DNA sequences are provided which encode the above-described rBPI protein and protein fragment products, including analog products. Such DNA sequences may also encode the 31-residue BPI leader sequence and the BPI polyadenylation signal. Also provided are autonomously-replicating DNA plasmid vectors which include DNA encoding the above-mentioned products and analogs as well as host cells which are stably transformed or transfected with that DNA in a manner sufficient to allow their expression. Transformed or transfected host cells according to the invention are of manifest utility in methods for the large-scale production of rBPI protein products of the invention.

The invention also contemplates rBPI protein analog products in the form of fusion proteins comprising, at the amino terminal, rBPI protein analog products of the invention and, at the carboxy terminal, a constant region of an immunoglobulin heavy chain or an allelic variant thereof. Natural sequence BPI/immunoglobulin fusion proteins are taught in the co-pending, co-owned U.S. patent application Ser. No. 07/885,911 by Theofan, et al., the disclosures of which are incorporated herein by reference. The invention further contemplates methods for producing the aforementioned fusion proteins.

Also within the scope of the present invention are DNA sequences encoding biologically-active rBPI protein fragment products having from about 176 to about 198 of the N-terminal amino acids of BPI. These DNAs allow for production of BPI products in eukaryotic host cells, such as CHO cells, wherein the products display less heterogeneity in terms of the carboxy terminal residues present. Presently preferred are DNAs encoding 193 N-terminal residues of BPI (e.g., DNAs encoding the thirty-one amino acid leader sequence of BPI, the initial 193 N-terminal amino acids, and one or more stop codons). Most preferred are such DNAs which additionally encode proteins wherein the cysteine at either position 132 or 135 is replaced (e.g, rBPI(1-193)ala$^{132}$).

Finally, the present invention also provides stable, homogeneous pharmaceutical compositions comprising the rBPI protein products of the invention in pharmaceutically acceptable diluents, adjuvants, and carriers. Such pharmaceutical compositions are resistant to the formation of rBPI product particles. Such compositions are useful in the treatment of gram-negative bacterial infection and the sequelae thereof, including endotoxin-related shock and one or more conditions associated therewith, such as disseminated intravascular coagulation, anemia, thrombocytopenia, leukopenia, adult respiratory distress syndrome, renal failure, hypotension, fever, and metabolic acidosis.

Numerous additional aspects and advantages of the invention will become apparent to those skilled in the art upon considering the following detailed description of the invention which describes presently preferred embodiments thereof.

DETAILED DESCRIPTION

Figure 1:
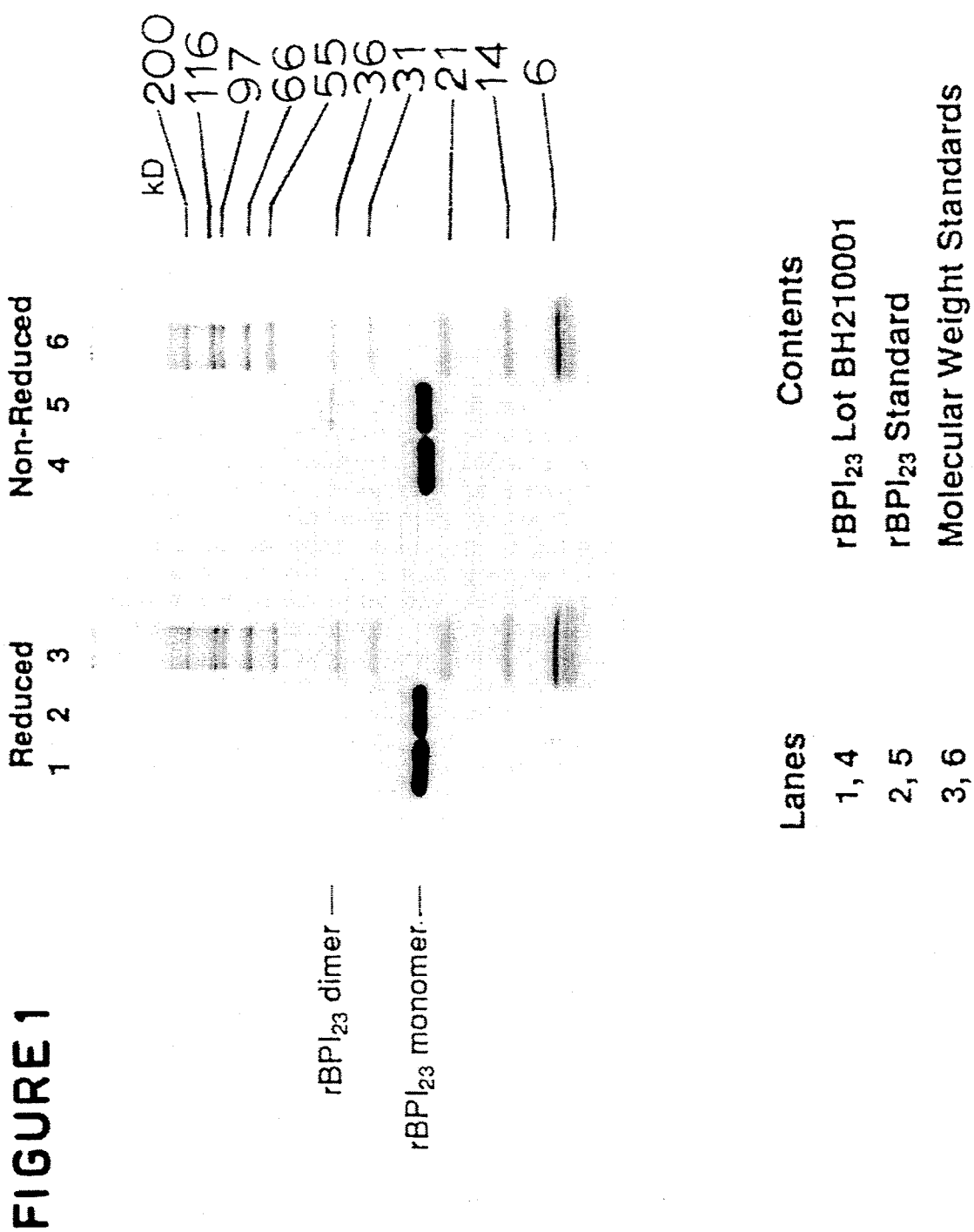
FIG. 1 represents results of SDS-PAGE analysis of rBPI(1-199) products.

The following detailed description relates to the manufacture and properties of various rBPI product preparations which comprise an amino acid substitution at a cysteine residue and/or highly uniform carboxy termini. More specifically, Example 1 relates to an exemplary means by which base substitutions are introduced in the nucleotide sequence encoding an exemplary N-terminal fragment of the BPI protein and to the incorporation of such mutated sequences into plasmid vectors. Example 2 addresses the incorporation of vectors of Example 1 into appropriate host cells and further describes the expression of recombinant BPI protein polypeptide products of the invention. Example 3 relates to construction of DNAs encoding cysteine replacement analog products of the invention and the use thereof in in vitro transcription/translation procedures. Example 4 relates to properties of rBPI product polypeptides of the invention.

EXAMPLE 1

Construction of Vectors Containing BPI Cysteine Replacement Analogs

A. Construction of Plasmids pING4519 and pING4520

The expression vector, pING4503, was used as a source of DNA encoding a recombinant expression product designated rBPI(1–199), i.e., encoding a polypeptide having the 31-residue signal sequence and the first 199 amino acids of the N-terminus of the mature human BPI, as set out in SEQ ID NOs: 1 and 2 except that valine at position 151 is specified by GTG rather than GTC and residue 185 is glutamic acid (specified by GAG) rather than lysine (specified by AAG).

Plasmid pING4503 has been described in co-pending, co-owned U.S. patent application Ser. No. 07/885,911 by Theofan, et al. which is incorporated herein by reference with respect to the background of the invention. Briefly, the construction of pING4503 is based on plasmid pING2237N which contains the mouse immunoglobulin heavy chain enhancer element, the LTR enhancer-promoter element from Abelson murine leukemia virus (A-MuLv) DNA, the SV40 19S/16S splice junction at the 5' end of the gene to be expressed, and the human genomic gamma-1 polyadenylation site at the 3' end of the gene to be expressed. Plasmid pING2237N also has a mouse dihydrofolate reductase (DHFR) selectable marker. The DNA encoding rBPI(-1–199), including 30 bp of the natural 5' untranslated region and bases encoding the 31 amino acid signal sequence, as well as 199 N-terminal amino acids of BPI, is inserted between unique SalI and SstII restriction sites in pING4503.

Two vectors, pING4519 and pING4520, were constructed based on pING4503 for expression of rBPI(-1–199) cysteine replacement analogs in which one of the three naturally-occurring cysteine residues of BPI was replaced with another amino acid. A PvuII site (CAGCTG) which occurs only once in the DNA encoding rBPI(1–199), and which is located between cysteine 132 and cysteine 135, was utilized in these constructions. Because several additional PvuII sites exist in pING4503, it was first necessary to isolate the SalI-SstII fragment which contained the insert encoding rBPI(1–199) from pING4503 by digesting with SalI and SstII. The purified SalI-SstII rBPI(1–199) insert was then digested with PvuII, resulting in an approximately 529 bp SalI-PvuII fragment and an approximately 209 bp PvuII-SstII fragment, each of which was purified separately.

Plasmid pING4519 is identical to pING4503 except that pING4519 contains a DNA insert encoding an rBPI(1–199) in which a codon for alanine is substituted for the codon specifying the native cysteine at position 132. As noted above, the recombinant product resulting from host cell expression and secretory processing of such an insert is referred to as "rBPI(1–199)ala$^{132}$". In order to generate pING4519, BPI DNA sequences were PCR amplified from pING4503 using the primers BPI-6: AAGCTTGTCGACCAGGCCTTGAGGT (SEQ ID NO: 3), which incorporated a SalI restriction site at the 5' end of the 30 bp BPI untranslated region, and BPI-14: CTGGAGGCGGTGATGGTG (SEQ ID NO: 4), which incorporated one half of the PvuII site and the base substitutions necessary to code for alanine at position 132. PCR amplification was accomplished using the GeneAmp PCR kit (Perkin Elmer Cetus, Norwalk, Conn.) according to the manufacturer's instructions. The resulting PCR fragment was digested with SalI, resulting in an approximately 529 bp SalI-blunt fragment which was then used in a three-piece ligation, together with the approximately 209 bp PvuII-SstII fragment described above and the large fragment resulting from SalI and SstII digestion of pING4503, to generate pING4519.

Plasmid pING4520 is identical to pING4519 with the exception that pING4520 contains a DNA insert encoding an rBPI(1–199) analog in which a serine codon is substituted for the codon specifying the native cysteine at position 135. As noted above, the recombinant product resulting from host cell expression of such an insert is designated "rBPI(1–199)ser$^{135}$". In order to generate pING4520, BPI DNA sequences were PCR amplified from pING4513, a plasmid essentially similar to pING4503 except that the selection marker is gpt instead of DHFR and the cDNA insert encodes the signal sequence and full-length BPI (456 residues) instead of only the rBPI(1–199) portion.

Amplification by PCR was accomplished using primer BPI-15: CTCCAGCAGCCACATCAAC (SEQ ID NO: 5), wherein the 5' end incorporates one half of a mutated PvuII site (wherein "CTG" is changed to "CTC") and the base substitutions necessary to code for serine at position 135; and primer BPI-7: GAACTTGGTTGTCAGTCG (SEQ ID NO: 6), representing rBPI-encoding sequences located downstream of the region encoding BPI residue 199. This PCR fragment was digested with BstBI, which cuts downstream of the cysteine 135 mutagenesis site, and the resulting approximately 100 bp blunt-BstBI fragment was gel purified. A three piece ligation was then performed with the 529 bp SalI-PvuII BPI restriction fragment described above, the 100 bp blunt-BstBI fragment, and a large fragment resulting from BstBI-SalI digestion of pING4503, to generate pING4520.

B. Construction of Plasmid pING4530

Another vector, pING4530, was constructed which contained the alanine-for-cysteine replacement as in pING4519, but which contained the gpt selectable marker (allowing for mycophenolic acid resistance) instead of the DHFR marker carried over from pING4503 to pING4519. To construct pING4530, a 1629 bp SalI-DraIII restriction fragment was isolated from pING4519. This fragment included all of the rBPI(1-199)ala$^{132}$ coding region as well as an additional approximately 895 bp vector sequence at the 3' end of the coding region. This fragment was ligated to the large (approximately 7230 bp) DraIII-SalI vector fragment isolated from pING4513 to generate pING4530.

C. Construction of Plasmid pING4533

Plasmid pING4533 was constructed for expression of rBPI(1-199)ala$^{132}$, wherein the codon specifying the fifth amino acid of the BPI signal sequence, methionine (ATG), at position −27 was placed in the context of the consensus Kozak translation initiation sequence GCCACCRCCATGG (SEQ ID NO: 7) [Kozak, *Nucl. Acid. Res.*, 15:8125 (1987)], and in which the DNA sequence encoding the first 4 amino acids of the BPI signal was removed. This was accomplished by PCR amplification of BPI sequences from a plasmid containing the full length human BPI cDNA [in pGEM-7zf(+)] using the PCR primer BPI-23: ACTGT-CGACGCCACCATGGCCAGGGGC (SEQ ID NO: 8), incorporating a SalI restriction site and the nucleotides GCCACC in front of the ATG (methionine) at position −27 of the BPI signal, and the primer BPI-2: CCGCGGCTCGAGCTATATTTTGGTCAT (SEQ ID NO: 9), corresponding to the 3' end of the rBPI(-1-199) coding sequence.

The approximately 700 bp PCR amplified DNA was digested with SalI and EcoRI and the resulting 270 bp fragment, including approximately the first one-third of the BPI(1-199) coding sequence, was purified. This SalI-EcoRI fragment was ligated to 2 other fragments: (1) a 420 bp EcoRI-SstII fragment from pING4519, encoding the remainder of BPI(1-199) wherein alanine replaces cysteine at position 132; and (2) an approximately 8000 bp SstII-SalI vector fragment from pING4502 (a vector essentially similar to pING4503 except that it does not include the 30 bp 5' untranslated sequence and has a gpt marker rather than DHFR), to generate pING4533 which contains a gpt marker.

D. Construction of Plasmids pING4221, pING4222, and pING4223

Vectors similar to pING4533 were constructed having an insert which contained the optimized Kozak translation initiation site corresponding to methionyl residue −27 of the signal sequence, and an alanine-for-cysteine replacement at position 132. However, the BPI fragment coding sequence terminated at residue 193 in these constructions. As noted above, the recombinant product resulting from host cell expression of this DNA is referred to as "rBPI(1-193)ala$^{132}$". Vectors containing these inserts were made by first digesting pING4533 with SalI, which cuts at the 5' end of the BPI DNA insert, and AlwNI, which leaves a three bp 3'-overhang at residue 192. The resulting approximately 700 bp fragment was then purified. This fragment was re-ligated into the large fragment resulting from pING4533 digestion with SstII-SalI, along with two annealed complementary oligonucleotides, BPI-30: CTGTAGCT-CGAGCCGC (SEQ ID NO: 10) and BPI-31: GGCTCGAGCTACAGAGT (SEQ ID NO: 11). This replaced the region between the AlwNI and SstII sites with the codon for residue 193 (leucine), a stop codon, and an XhoI restriction site 5' to the SstII site and resulted in regeneration of both the AlwNI and the SstII sites and placement of the stop codon, TAG, immediately after the codon (CTG) for amino acid 193 (leucine). The resultant plasmid was designated pING4223 and had the gpt marker. Similar constructions were made exactly as described for pING4223 except that different SstII-SalI vector fragments were used to generate vectors with different selection markers. For example, pING4221 is identical to pING4223 except that it contains the his marker (conferring resistance to histidinol) instead of gpt and pING4222 is identical to pING4223 except that it contains the DHFR marker instead of gpt.

E. Construction of Plasmids pING4537, pING4143, pING4146, pING4150, and pING4154

A series of vectors was constructed which contained an insert encoding rBPI(1-193)ala$^{132}$, the optimized Kozak translation initiation site, and different selection markers essentially identical to those described with respect to pING4221, pING4222 and pING4223 except that the human genomic gamma-1 heavy chain polyadenylation and transcription termination region at the 3' end of the SstII site was replaced with a human light chain polyadenylation sequence followed by mouse light chain (kappa) genomic transcription termination sequences. In collateral gene expression studies, the light chain polyadenylation signal and transcription termination region appeared to be responsible for 2.5-5 fold increases in BPI expression levels in Sp2/0 and CHO-K1 cells.

The aforementioned vectors were constructed by first constructing pING4537, a vector similar to pING4533 which contains the rBPI(1-199)ala$^{132}$ insert. However, pING4537 includes the human light chain polyadenylation sequences instead of the human heavy chain sequence. The mouse kappa 3' sequences were obtained from pING3170, an expression vector which encodes a human light chain cDNA and includes a mouse genomic light chain 3' transcription termination sequence. This was accomplished by digesting with SstI, which cuts 35 bp upstream of the mouse light chain stop codon, treating with T4 DNA polymerase to make the end blunt, then cutting with BamHI, and purifying an approximately 1350 bp fragment which includes the mouse kappa 3' sequences. The resulting fragment consists of approximately 250 bp of the 3' portion of the human light chain constant region cDNA and the polyadenylation signal followed by a BamHI linker as described in the construct called Δ8 in Lui et al., *J. Immunol.* 139: 3521, (1987). The remainder of the approximately 1350 bp fragment consists of a BglII-BamHI mouse kappa 3' genomic fragment [fragment "D" of Xu et al., *J. Biol. Chem.* 261:3838, (1986)] which supplies transcription termination sequences. This fragment was used in a 3-piece ligation with two fragments from pING4533: a 3044 bp fragment which includes all of BPI insert and part of vector obtained by digestion with SstII, T4 polymerase treatment, and NotI digestion (which includes all of BPI insert and part of vector), and an approximately 4574 bp BamHI-NotI fragment. The resulting vector, pING4537, is identical to pING4533 with the exception of the above-noted differences in the genomic 3' untranslated region.

Additional vectors containing the kappa 3' untranslated sequences were constructed using pING4537 as the source of the kappa 3' fragment. The kappa 3' untranslated sequences were isolated by digestion of pING4537 with XhoI (a unique site which occurs immediately after the BPI stop codon) and BamHI. The resulting approximately 1360 bp XhoI-BamHI fragment was used in a series of 3-piece ligations to generate the following four vectors, all of which have inserts encoding rBPI(1-193)ala$^{132}$ and which have the optimized Kozak translation initiation site at residue −27 of the signal: (1) pING4143 (gpt marker), obtained by ligating a pING4223 4574 bp BamHI-NotI fragment (gpt marker), a pING4223 NotI-XhoI BPI insert-containing fragment of approximately 3019 bp, and the pING4537 XhoI-BamHI fragment; (2) pING4146 (DHFR marker), obtained by ligating a pING4222 approximately 4159 bp BamHI-NotI fragment (DHFR marker), a pING4223 NotI-XhoI BPI insert-containing fragment of approximately 3019 bp, and the pING4537 XhoI-BamHI fragment; (3) pING4 150 (his marker), obtained by ligating a pING4221 his-containing approximately 4772 bp BamHI-NotI fragment, a pING4222 NotI-XhoI BPI insert-containing fragment, and the pING4537 XhoI-BamHI fragment; and (4) pING4154 (neo marker), obtained by ligating a pING3174 neo-containing approximately 4042 bp BamHI-BsaI fragment, a pING4221 BsaI-XhoI BPI insert-containing fragment of approximately 3883 bp and the pING4537 XhoI-BamHI fragment. Plasmid pING3174 contains an insert encoding antibody heavy chain DNA and has a neo marker. The neogene and its flanking sequences were obtained from the pSv2 neo plasmid reported by Southern et al., *J. Mol. Appl. Genet.*, 1:327 (1982).

F. Construction of Plasmids pING4144 and pING4151

Figure 3:
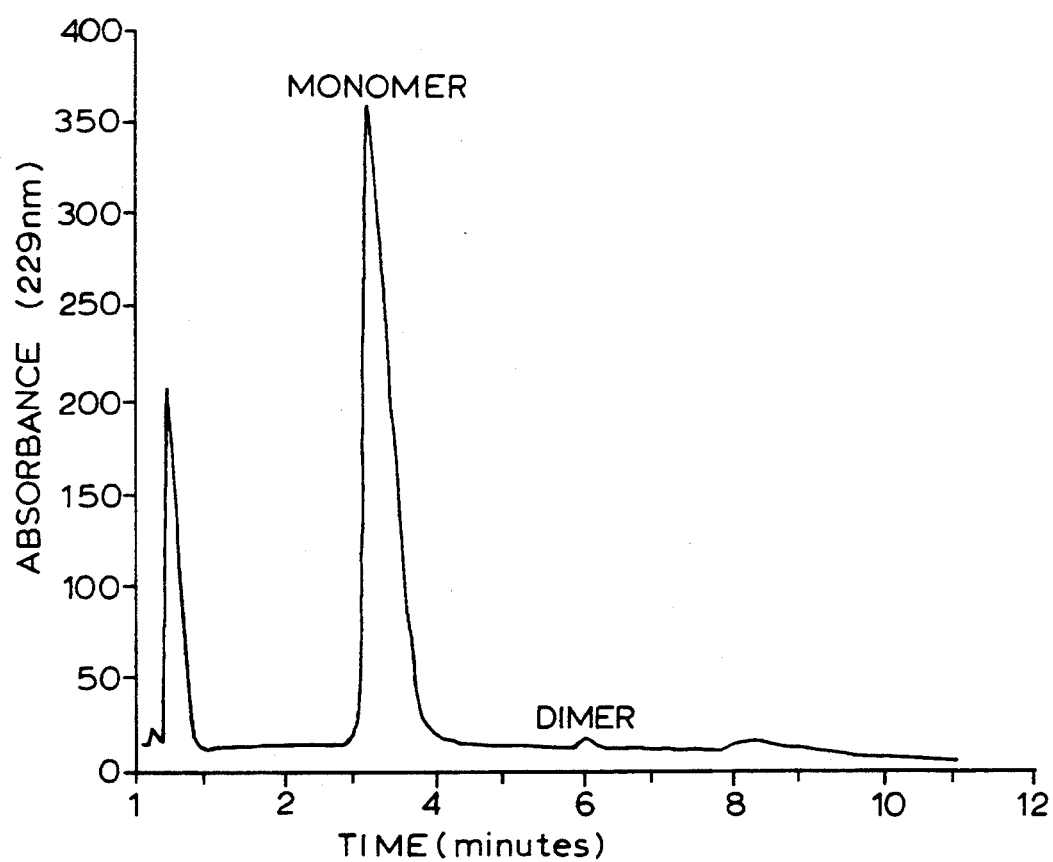
FIG. 3 depicts results of cation exchange HPLC analysis of rBPI(1-199) products.

Two plasmids were constructed, pING4144 and pING4151, which were identical to pING4143 and pING4150, respectively, except that expression of rBPI coding sequences was under control of the human cytomegalovirus (hCMV) immediate early enhancer/promoter instead of the Abelson murine leukemia virus (A-MuLv) LTR promoter. Therefore, both pING4144 and pING4151 contained the mutation of the cysteine at position 132 to alanine, the optimized Kozak translation initiation sequence, and the human light chain poly-A/mouse kappa genomic transcription termination region. The region between nucleotides 879 and 1708 of the original vectors (pING4143 and pING4 150) was replaced with a region of the hCMV enhancer/promoter corresponding to nucleotides −598 through +174 as shown in FIG. 3 of Boshart et al., *Cell* 41:521 (1985), incorporated herein by reference. To introduce the hCMV promoter region into BPI expression vectors, plasmid pING4538 was first constructed by replacing the approximately 1117 bp EcoRI-SalI/A-MuLv promoter-containing fragment of pING4222 with an approximately 1054 bp EcoRI-SalI/hCMV promoter-containing fragment from plasmid pING2250 which contains the hCMV promoter driving expression of an antibody light chain insert. To construct pING4 144, three fragments were ligated together: (1) the approximately 2955 bp rBPI(1-193)-containing NotI-XhoI fragment from pING4538; (2) the approximately 1360 bp XhoI-BamHI fragment from pING4537; and (3) the approximately 4770 bp BamHI-NotI fragment containing the his gene from pING4221.

G. Construction of Plasmids pING4145, pING4148 and pING4152

Plasmids pING4 145, pING4 148 and pING4 152 were constructed and were identical to pING4143, pING4146, and pING4 150, respectively, except that they contained the wild-type (natural sequence) cysteine at position 132 instead of an alanine substitution. Thus, all three contained the rBPI(1-193) insert, the optimized Kozak translation initiation sequence and the human light chain Poly A/mouse kappa genomic transcription termination region. These three plasmids were constructed as follows. To construct pING4145, three fragments were ligated together: (1) the approximately 3000 bp NotI-XhoI BPI(1-193) containing fragment from pING4140 (pING4140 is identical to pING4221 except that it contains the wild-type cysteine at Position 132); (2) the approximately 1360 bp XhoI-BamHI fragment from pING4537; and (3) the approximately 4570 bp BamHI-NotI fragment containing the gpt gene from pING4223. To construct pING4 148, three fragments were ligated together: (1) the NotI-XhoI fragment from pING4140; (2) the XhoI-BamHI fragment from pING4537; and (3) the approximately 4150 bp BamHI-NotI fragment containing the DHFR gene from pING4222. To construct pING4152, three fragments were ligated together: (1) the approximately 3000 bp NotI-XhoI fragment from pING4142 (pING4142 is identical to pING4223 except that it contains the wild-type cysteine at (2) the XhoI-BamHI fragment from pING4537; and (3) the approximately 4770 bp BamHI-NotI fragment containing the his gene from pING4221.

Table I, below, summarizes the content of the plasmids whose preparation is described in Sections A through G above.

TABLE I

| Plasmid | BPI Product | Signal Seq. | Marker | 3' Terminal | Promoter |
|---|---|---|---|---|---|
| pING4519 | (1-199)Ala$^{132}$ | 31AA | DHFR* | Human Genomic HC Gamma-1 Poly-A | A-MuLv |
| pING4520 | (1-199)Ser$^{135}$ | 31AA | DHFR* | Human Genomic HC Gamma-1 Poly-A | A-MuLv |
| pING4530 | (1-199)Ala$^{132}$ | 31AA | gpt | Human Genomic HC Gamma-1 Poly-A | A-MuLv |
| pING4533 | (1-199)Ala$^{132}$ | Kozak initiation Seq; 27AA signal | gpt | Human Genomic HC Gamma-1 Poly-A | A-MuLv |
| pING4223 | (1-193)Ala$^{132}$ | Kozak initiation Seq; 27AA signal | gpt | Human Genomic HC Gamma-1 Poly-A | A-MuLv |

TABLE I-continued

| Plasmid | BPI Product | Signal Seq. | Marker | 3' Terminal | Promoter |
|---|---|---|---|---|---|
| pING4221 | (1-193)Ala$^{132}$ | Kozak initiation Seq; 27AA signal | his | Human Genomic HC Gamma-1 Poly-A | A-MuLv |
| pING4222 | (1-193)Ala$^{132}$ | Kozak initiation Seq; 27AA signal | DHFR | Human Genomic HC Gamma-1 Poly-A | A-MuLv |
| pING4537 | (1-199)Ala$^{132}$ | Kozak initiation Seq; 27AA signal | gpt | Human Kappa Poly-A/Mouse Kappa Genomic Transcription Termination | A-MuLv |
| pING4143 | (1-193)Ala$^{132}$ | Kozak initiation Seq; 27AA signal | gpt | Human Kappa Poly-A/Mouse Kappa Genomic Transcription Termination | A-MuLv |
| pING4146 | (1-193)Ala$^{132}$ | Kozak initiation Seq; 27AA signal | DHFR | Human Kappa Poly-A/Mouse Kappa Genomic Transcription Termination | A-MuLv |
| pING4150 | (1-193)Ala$^{132}$ | Kozak initiation Seq; 27AA signal | his | Human Kappa Poly-A/Mouse Kappa Genomic Transcription Termination | A-MuLv |
| pING4144 | (1-193)Ala$^{132}$ | Kozak initiation Seq; 27AA signal | gpt | Human Kappa Poly-A/Mouse Kappa Genomic Transcription Termination | hCMV |
| pING4145 | (1-193) | Kozak initiation seq; 27AA signal | gpt | Human Kappa Poly-A/Mouse Kappa Genomic Transcription Termination | A-MuLv |
| pING4148 | (1-193) | Kozak initiation Seq; 27AA signal | DHFR | Human Kappa Poly-A/Mouse Kappa Genomic Transcription Termination | A-MuLv |
| pING4152 | (1-193) | Kozak initiation Seq; 27AA Signal | his | Human Kappa Poly-A/Mouse Kappa Genomic Transcription Termination | A-MuLv |
| pING4151 | (1-193)ala$^{132}$ | Kozak initiation Seq; 27AA signal | his | Human Kappa Poly-A/Mouse Kappa Genomic Transcription Termination | hCMV |
| pING4154 | (1-193)ala$^{132}$ | Kozak initiation Seq; 27AA signal | neo | Human Kappa Poly-A/Mouse Kappa Genomic Transcription | A-MuLv |

TABLE I-continued

| Plasmid | BPI Product | Signal Seq. | Marker | 3' Terminal Termination | Promoter |
| --- | --- | --- | --- | --- | --- |

*An altered DHFR gene as described in co-pending, co-owned U.S. Pat. application, Ser. No. 07/885,911, incorporated herein by reference.

EXAMPLE 2

Transfection of Cells for Expression of the rBPI Cysteine Replacement Analogs

Mammalian cells are preferred hosts for production of rBPI protein analogs according to the invention because such cells allow for proper secretion, folding, and post-translational modification of expressed proteins. Presently preferred mammalian host cells for production of analogs of the invention include cells of fibroblast and lymphoid origin, such as: CHO-K1 cells (ATCC CCL61); CHO-DG44 cells, a dihydrofolate reductase deficient [DHFR−] mutant of CHO Toronto obtained from Dr. Lawrence Chasin, Columbia University; CHO-DXB-11, a DHFR− mutant of CHO-K1 obtained from Dr. Lawrence Chasin; Vero cells (ATCC CRL81); Baby Hamster Kidney (BHK) cells (ATCC CCL10); Sp2/O-Ag14 hybridoma cells (ATCC CRL1581); and NSO myeloma (ECACC No. 85110503).

Transfection of mammalian cells may be accomplished by a variety of methods. A common approach involves calcium phosphate precipitation of expression vector DNA which is subsequently taken up by host cells. Another common approach, electroporation, causes cells to take up DNA through membrane pores created by the generation of a strong electric field [(Sambrook et al., *Molecular Cloning, A Laboratory Manual,* Cold Spring Laboratory Harbor Press, 16.30–16.31 (1989)]. Selection for transfected cells is facilitated by incorporation in the expression vector of a gene whose product allows the transfected cells to survive and grow under selective conditions. A number of such genes have been identified. These include, among others: (1) neo, a prokaryotic gene which encodes resistance to the aminoglycoside antibiotic G418; (2) *E. coli* guanine phoshporibosyl transferase (gpt), which encodes resistance to mycophenolic acid (MPA) in the presence of xanthine, [Mulligan et al., *Proc. Nat. Acad. Sci. U.S.A.,* 78:2072–2076 (1981)]; (3) dihydrofolate reductase (DHFR), which allows for growth of DHFR− cells in the absence of nucleosides and gene amplification in the presence of increasing concentration of methotrexate; (4) the hisD gene of *Salmonella typhimurium* which allows growth in the presence of histidinol [Hartman et al., *Proc. Nat. Acad. Sci. U.S.A.,* 85:8047–8051, (1988)]; (5) the trpB gene of *E. coli* [Hartman et al., *Proc. Nat. Acad. Sci. U.S.A.,* 85:8047–8051, (1988)], which allows growth in the presence of indole (without tryptophan); and (6) the glutamine synthetase gene, which allows growth in media lacking glutamine. The availability of these selective markers, either alone or in various combinations, provides flexibility in the generation of mammalian cell lines which express recombinant products at high levels.

A. Transfection of CHO-K1 Cells with pING4533

Plasmid pING4533 contains gene sequences encoding rBPI(1–199)ala$^{132}$ fused to the A-MuLv promoter, the optimized Kozak translation initiation sequence, the human gamma-1 heavy chain 3' untranslated region, and the gpt marker for selection of MPA-resistant cells.

The CHO-K1 cell line is maintained in Ham's F12 medium plus 10% fetal bovine serum (FBS) supplemented with glutamine/penicillin/streptomycin (Irvine Scientific, Irvine, Calif.). The cells were transfected by electroporation with 40 μg of pING4533 DNA which was first digested with NotI, extracted with phenol-chloroform and ethanol precipitated. Following electropotation, the cells were allowed to recover for 24 hours in non-selective Ham's F12 medium. The cells were then trypsinized, resuspended at a concentration of $5 \times 10^4$ cells/ml in Ham's F12 medium supplemented with MPA (25 μg/ml) and xanthine (250 μg/ml) and then plated at $10^4$ cells/well in 96-well plates. Untransfected CHO-K1 cells are unable to grow in this medium due to the inhibition of pyrimidine synthesis by MPA.

At 2 weeks, colonies consisting of transfected cells were observed in the 96-well plates. Supernatants from wells containing single colonies were analyzed for the presence of BPI-reactive protein by anti-BPI ELISA using rBPI(1–199) as a standard. In this assay, Immulon-II 96-well plates (Dynatech, Chantilly, Va.) were precoated with affinity purified rabbit anti-rBPI(1–199) antiserum. Supernatant samples were added and detection was carried out using affinity purified, biotinylated rabbit anti-rBPI(1–199) antiserum and peroxidase-labeled avidin.

Approximately 800 colonies were screened in this manner. Thirty-one colonies having the highest production were transferred to 24-well plates for productivity assessment. Cells were grown to confluence in a 24-well plate in Ham's F12 medium supplemented with 10% FBS. Once the cells reached confluence, the Ham's F12 medium was removed and 1 ml of HB-CHO serum free medium (Irvine Scientific) plus 40 μl of sterile S-sepharose beads (Pharmacia, Piscataway, N.J.) was added as in co-owned, co-pending U.S. patent application Ser. No.07/885,501 by Grinna. The cells were then incubated for 7 days after which the S-sepharose beads were removed and washed with 0.1M NaCl in 10 mM Tris buffer (pH7.5). The product was eluted from the beads by addition of 1.0M NaCl in Tris buffer and quantitated by ELISA as described above. The top-producing transformant, designated A153, secreted approximately 3 μg/ml in this assay and was adapted to growth in Excell 301 serum-free medium (JRH Scientific, Lenexa, Kans.). The adapted cells were grown in 1.5 L fermenters in Excell 301 medium in the presence of Ssepharose beads. Productivity was assessed at 120–140 hours by C4 HPLC analysis of product eluted from S-sepharose beads (50 ml aliquots). The productivity was 15–25 μg/L at these stages of the fermentation.

B. Transfection of CHO-DG44 Cells with pING4222

Plasmid pING4222 contains DNA encoding the rBPI(1–193)ala$^{132}$ analog fused to the A-MuLv promoter, optimized Kozak initiation sequence, human gamma-1 heavy chain 3' untranslated region, and the mouse DHFR gene for selection of transfected cells in a nucleoside-free medium.

The cell line, CHO DG44, was maintained in Ham's F12 medium plus 10% FBS with glutamine/penicillin/-streptomycin. The cells were transfected with linearized pING4222 DNA (40 μg digested with PvuI, phenol-chloroform extracted, ethanol precipitated) using the calcium phosphate method of Wigler, et al. *Cell*, 11:223 (1977). Following calcium phosphate treatment, the cells were plated in 96-well plates at approximately $10^4$ cells/well and transfectants were obtained by growth in selective medium consisting of αMEM medium lacking nucleosides (Irvine Scientific) and supplemented with dialyzed FBS (100 ml serum dialyzed vs 4L cold 0.15M NaCl using 6000–8000 MW cutoff, 16 hours, 4° C.). Untransfected CHO-DG44 cells are unable to grow in this medium due to the DHFR mutation and the lack of nucleosides in the medium supplemented with dialyzed serum.

At 2 weeks, each well contained approximately 2–3 colonies. The supernatants from wells of a 96-well plate were analyzed for the presence of rBPI(1–193)ala$^{132}$ by ELISA as in Section A. Twenty-four highest-producing clones were expanded into 24-well plates in selective αMEM medium supplemented with 0.05 μM methotrexate to induce gene amplification of the rBPI analog-encoding DNA. On observation of growth, cells were transferred to a new 24-well plate and productivity was assessed from S-sepharose eluates as described in section A for the pING4533/CHO-K1 transfectants. The five highest-producing clones were combined and subcloned by limiting dilution in 96-well plates. The supernatant wells containing single colonies were assayed for levels of rBPI(1–193)ala$^{132}$ by ELISA. Twenty highest-producing subclones were next expanded into 24-well plates and subjected to further amplification in the presence of 0.4 μM methotrexate and the levels of product expression for the amplified cells was determined by ELISA. The top producers, Clones 4, 75, and 80, secreted 25–37 μg/ml at 7 days in a 24-well plate containing S-sepharose.

C. Transfection of Sp2/O Cells with pING4223 and pING4221

A strategy adopted in an attempt to achieve optimal expression of desired rBPI products involved transfection of cells having a first expression plasmid with a first marker, screening for the highest producers, and then transfecting the same cells with a second expression plasmid having a different marker. This strategy is described below using Sp2/O cells.

Plasmid pING4223 contains DNA encoding rBPI(-1–193)ala$^{132}$ BPI fused to the A-MuLv promoter, optimized Kozak translation initiation sequence, human gamma-1 heavy chain 3' untranslated sequences, and the gpt marker for selection of MPA-resistant cells.

The Sp2/O cell line was maintained in DMEM medium supplemented with 10% FBS with glutamine/penicillin/streptomycin. The Sp2/0 cells were transfected by electroporation with 40 μg of pING4223 DNA which had been digested with NotI, extracted with phenol-chloroform and ethanol precipitated. Following electroporation, the cells were allowed to recover for 48 hours in non-selective DMEM medium. The cells were then centrifuged and resuspended at a concentration of $5 \times 10^4$ cells/ml in DMEM medium supplemented with MPA (6 μg/ml) and xanthine (250 μg/ml) and plated at $10^4$ cells/well in 96-well plates. Untransfected Sp2/0 cells are unable to grow in this medium due to the inhibition of pyrimidine synthesis by the MPA. At 1.5–2 weeks, colonies consisting of transfected cells were observed in the 96-well plates. Supernatants from wells containing single colonies were analyzed for the presence of product-reactive protein by ELISA. The highest producers were transferred to a 24-well plate and productivity was assessed in extinct 24-well cultures for cells grown in the presence and absence of $10^{-7}$M dexamethasone, which causes an increase in expression by the A-MuLv promoter as a result of interactions with the glucocorticoid receptor. The best producer, Clone 2×3, secreted approximately 3 μg/ml and 7 μg/ml in the absence and presence of dexamethasone, respectively.

Clone 2×3 was next transferred by electroporation with pING4221, which contains the his gene for selection of transfectants. Following recovery for 48 hours in DMEM plus 10% FBS medium, the cells were plated in 96-well plates at approximately $10^4$ cells/well in DMEM/FBS supplemented with 6 μg/ml MPA, 250 μg/ml xanthine and 8 mM histidinol. Untransfected cells were unable to grow in the presence of the histidinol and MPA. At 1.5–2 weeks, transfected cells were observed in the 96-well plates. Supernatants from wells containing single colonies were analyzed for the presence of rBPI-reactive protein by ELISA.

The highest producers were transferred to a 24-well plate. Productivity was assessed as extinct 24-well cultures for cells grown in the presence and absence of $10^{-7}$M dexamethasone. The best producer, Clone 2×3-130, secreted approximately 15 μg/ml and 30 μg/ml in the absence and presence of dexamethasone, respectively. This isolate was next subcloned by limiting dilution in 96-well plates. Wells containing single colonies were screened by ELISA and the best producers were expanded and retested in 24 well cultures in the presence and absence of $10^{-7}$M dexamethasone. The highest producing subclone, No. 25, secreted approximately 16 μg/ml and 33 μg/ml in the absence and presence of dexamethasone, respectively.

D. Transfection of Sp2/0 Cells with pING4 143 and pING4150

Plasmid pING4143 contains DNA encoding rBPI(-1–193)ala$^{132}$ fused to the A-MuLv promoter, optimized Kozak translation initiation sequence, and mouse kappa light chain 3' untranslated sequences along with the gpt gene for selection of MPA-resistant cells. The Sp2/0 cells were transfected by electroporation with 40 μg of pING4143 DNA that was first digested with NotI, phenol-chloroform extracted, and ethanol precipitated. Following electroporation, the cells were allowed to recover for 48 hours in non-selective DMEM medium. The cells were then centrifuged and resuspended at a concentration of $5 \times 10^4$ cells/ml in DMEM medium supplemented with MPA (6 μg/ml) and xanthine (250 μg/ml) and plated at approximately $10^4$ cells/well in 96-well plates.

At approximately 2 weeks, colonies consisting of transfected cells were observed in the 96-well plates. Supernatants from wells containing single colonies were analyzed for the presence of BPI-reactive protein by ELISA. The highest producers were transferred to a 24-well plate. Productivity was assessed as extinct 24-well cultures for cells grown in the presence and absence of $10^{-7}$M dexamethasone. The best producer, Clone 134, secreted approximately 12 μg/ml and approximately 28 μg/ml in the absence and presence of dexamethasone, respectively.

Clone 134 was transfected by electroporation with the vector, pING4150, which contains DNA encoding rBPI(1–193)ala$^{132}$ fused to the A-MuLv promoter and mouse light chain 3' untranslated region with the his gene for selection of transfectants. Prior to electroporation, the vector was first digested, and phenol-chloroform-extracted and ethanol precipitated. Following recovery for 48 hours in DMEM plus 10% FBS medium, the cells were plated in 96-well plates at approximately $10^4$ cells/well in DMEM/FBS supplemented with 6 μg/ml MPA plus 250 μg/ml xanthine and 8 mM histidinol. Untransfected cells are unable to grow in the presence of MPA and histidinol. At approximately 2 weeks, colonies consisting of transfected cells were observed in the 96-well plates. Supernatants from wells containing single colonies were analyzed for the presence of BPI-reactive protein by ELISA. The highest producers were transferred to a 24-well plate. Productivity was assessed as extinct 24 well cultures for cells grown in the presence and absence of $10^{-7}$M dexamethasone. The highest producer, Clone 134-11, was re-designated C1770. Clone C1770 secreted 36 μg/ml without dexamethasone and greater than 42 μg/ml in the presence of dexamethasone. This clone (c1770) was deposited with the American Type Culture Collection, 12301 Parklawn Drive, Rockville, Md. 20852 as Accession No. HB 11247.

E. Transfection of CHO-K1 Cells with pING4143

The CHO-K1 cell line was transfected with pING4143 DNA in the manner described in Section A for transfection of CHO-K1 cells with pING4533. At approximately 2 weeks, supernatants from approximately 800 wells containing single colonies were analyzed for the presence of BPI-reactive protein by ELISA. The top producers were transferred to 24-well plates. The top producers, secreting approximately 9–13 μg/ml, may next be adapted to serum-free medium in preparation for growth in fermenters. These may also be re-transfected with a vector, such as pING4150 or pING4154 with his or neo as selective markers, respectively, to provide a cell line which produces even higher levels of rBPI product.

F. Transfection of CHO-K1 Cells with pING4144

Plasmid pING4144 is similar to pING4143 except that it contains the human cytomegalovirus (hCMV) promoter instead of the A-MuLv promoter. The CHO-K1 cell line was transfected with pING4144 DNA in the manner described above in Section A. At approximately 2 weeks, supernatants from approximately 200 wells containing single colonies were analyzed for the presence of BPI-reactive protein by ELISA. The top producers were transferred to 24-well plates and rBPI expression determined in 24-well plates containing sodium butyrate. The top producer (clone 174) secreted approximately 3–5 μg/ml without butyrate and approximately 15–18 μg/ml in the presence of 5 mM butyrate in this assay. This clone, re-designated clone C1771, was deposited with the American Type Culture Collection, 12301 Parklawn Drive, Rockville, Md. 20852 as ATCC accession No. CRL 11246. Top producers may next be adapted to serum-free medium in preparation for growth in fermenters. These may also be re-transfected with a vector, such as pING4151 or pING4155, containing the rBPI gene under control of the hCMV promoter, but with his or neo as selective markers, respectively, to provide a cell line which produces even higher levels of BPI.

G. Transfection of NSO Cells with pING4143

NS0 cells were transfected with pING4143 DNA by electroporation. At approximately 3 weeks, colonies consisting of transfected cells were observed in the 96-well plates. Supernatants from wells containing single colonies were analyzed for the presence of BPI-reactive protein by ELISA. The highest producers were transferred to a 24-well plate. Productivity was assessed as extinct 24-well cultures. The highest producers secreted a 15–16 μg/ml. The highest producers may be retransfected with a vector, such as pING4150, as described above to yield even higher producers.

H. Transfection of NS0 Cells with pING4232

NS0 cells were transfected by electroporation with pING4132, which contains DNA encoding rBPI(1-19-3)ala$^{132}$ fused to the optimal Kozak translation initiation sequence cloned into the vector pEE13 [Bebbington, et al. *Biotechnology*, 10: 169–175 (1992)]. Vector pEE13 contains the glutamine synthetase gene for selection of transfectants which are able to grow in medium lacking glutamine. At approximately three weeks, colonies consisting of transfected cells were observed in 96-well plates. Supernatants from wells containing single colonies were analyzed by ELISA. The highest producers were transferred to a 24-well plate. Productivity was assessed as extinct 24-well cultures. The highest producers, secreting 7–15 μg in extinct 24 well-cultures, may next be subjected to amplification in the presence of various concentrations of methionine sulfoximine.

I. Transfection of Sp2/0 Cells with pING4145

Plasmid pING4145 contains DNA encoding rBPI(-1-193)ala$^{132}$ fused to the A-MuLv promoter, optimized Kozak translation initiation sequence, mouse kappa light chain 3' untranslated sequences, and a gpt gene for selection of MPA-resistant cells. The Sp2/0 cells were transfected by electroporation with 40 μg of pING4145 DNA that was first digested with NotI, phenol-chloroform extracted, and ethanol precipitated. Following electroporation, the cells were allowed to recover for 48 hours in non-selective DMEM medium, centrifuged, and resuspended at a concentration of $5 \times 10^4$ cells/ml in DMEM medium supplemented with MPA (6 μg/ml) and xanthine (250 μg/ml). The cells may then be plated at approximately $10^4$ cells/well in 96-well plates. At approximately 2 weeks, colonies consisting of transfected cells are observed in the 96-well plates. Supernatants from wells containing single colonies may then be analyzed for the presence of BPI-reactive protein by ELISA. The highest producers are transferred to a 24-well plate and productivity is assessed as extinct 24-well cultures for cells grown in the presence and absence of $10^{-7}$M dexamethasone.

In order to maximize the expression of BPI, the highest producing Sp2/0 transfectant may be transfected by electroporation with a vector which contains gene sequences encoding rBPI(1-193)ala$^{132}$ fused to the A-MuLv promoter and mouse light chain 3' untranslated region with the his gene for selection of transfectants.

J. Transfection of CHO-K1 Cells with pING4145

The CHO-K1 cell line was transfected with pING4145 DNA in the manner described above in Section A. At approximately 2 weeks, supernatants from approximately 500–800 wells containing single colonies may be analyzed for the presence of BPI-reactive protein by ELISA. The top producers are transferred to 24-well plates and BPI expression determined in 24-well plates containing S-sepharose. The top producers are next adapted to serum-free medium in preparation for growth in fermenters. These may also be re-transfected with a vector containing a different selective marker to provide a cell line which produces even higher levels of rBPI product.

K. Expression of rBPI Products from Insect Cells

Another eukaryotic system in which rBPI products may be expressed is insect cells which have been infected with a recombinant baculovirus containing DNA encoding an rBPI product. Systems for generating recombinant virus and for achieving expression of recombinant products therefrom are commercially available (Invitrogen, San Diego, Calif.). DNA encoding rBPI(-1-199), including the 31 amino acid signal sequence, was cloned into an NheI site in a pBlueBac transfer vector (Invitrogen). Sf9 insect cells (BRL; ATCC CRL 1711) were co-transfected with this vector and with wild type AcMNPV (*Autographa californica* multiple nuclear polyhidrosis virus, Invitrogen). Recombinant viral plaques were then identified, purified, and used to generate high-tiler recombinant viral stocks as described in protocols available from BRL.

The recombinant-produced baculovirus was used to infect further Sf9 cells. To do this, 8 separate 60 mm dishes of Sf9 cells were infected with the baculovirus. Each of the 8 dishes was sampled at different times during the day by collecting medium from a dish of infected cells. Upon collection, the medium was centrifuged at 1000 rpm for 10 minutes and the supernatant was stored at 4° C. Cells were then rinsed once with 4 ml PBS and lysed with 100 µl/dish NP40 lysis buffer (1% NP40, 150 mM NaCl, 50 mM Tris-HCl, pH 8.0) by incubating on ice for 30 minutes. Cells were then collected into an Eppendorf tube with a cell scraper. Cell lysates were then spun in a microfuge for 2 minutes. The lysate supernatant was transferred to a new tube and stored at −20° C. Media samples from each daily time point were analyzed for BPI content by ELISA and lysates were analyzed by Western using an anti-BPI antibody.

No rBPI product was detectable in the media by ELISA on days 1–4 post-infection. However, on days 5–6 post-infection, a peak of 200–500 ng/ml rBPI product was detected in media samples. Western analysis of the lysates showed a BPI-reactive band of approximately 23 Kd at day 2 post-infection. That band showed increasing intensity through day 6.

Table II, below, summarizes the transfections detailed in Sections A–J above.

TABLE II

| Host Cell | Transfected With |
| --- | --- |
| CHO-DG44 | pING4222 |
| CHO-K1 | pING4533, pING4143, pING4144, pING4145 |
| NSO | pING4143, pING4232 |
| SP2/0 | pING4223 followed by pING4221, pING4143 followed by pING4150, pING4145 |

EXAMPLE 3

Construction of Plasmids for in vitro Transcription and Translation of rBPI(1–199)ala[132] and rBPI(1–199)Ser[135]

In vitro transcription/translation studies were conducted using plasmid pIC127 as a source of DNA encoding rBPI (1–199). Construction of pIC127 was carried out as follows. DNA encoding rBPI (1–199), including the 31-amino acid signal sequence, was PCR amplified from a plasmid containing full-length cDNA encoding BPI in pGEM-72f(+). The amplification was done such that a SalI site was incorporated at the 5' end and XhoI and SstII sites were incorporated at the 3' end of the rBPI-encoding sequence by using the primers BPI-3: GTCGACGCATGCGAGAGAACATGGC (SEQ ID NO: 12) and BPI-2: CCGCGGCTCGAGC-TATATTTTGGTCAT-(SEQ ID NO: 9). The resulting PCR amplified fragment was blunt-end cloned into the SmaI site of the multiple cloning region of plasmid pT7T3 18u (Pharmacia LKB Technology, Piscataway N.J.) in order to generate pIC102.

The pIC102 insert encoding rBPI (1–199) and the 31-amino acid signal were then excised by digestion of the plasmid with BamHI and Asp718I. A BamHI site flanks the SalI site in pIC102 and an Asp718I site flanks the SstII site in pIC102. The ends of the excised fragment were made blunt with T4 DNA polymerase and the blunt fragment was then cloned into plasmid pGEM1 (ProMega, Madison, Wisc.) which had first been digested with PstI and EcoRI and blunted with T4 DNA polymerase. The resulting construction was designated pIC124 and has the rBPI (1–199)-encoding insert oriented such that its 5' end is adjacent to the Sp6 promoter in pGEM1.

The 31-amino acid signal sequence in the pIC124 insert was then excised by removing the region between two HincII sites in pIC124 to create pIC127. The excised region was replaced with a linker which restored the initiation codon (ATG) and the sequence encoding the first amino acid of BPI. Two fragments were isolated from pIC124 digestion with HincII and SstII: (1) the HincII-SstII fragment containing the rBPI (1–199)-coding region excluding the codon for the first amino acid; and (2) the SstII-HincII fragment comprising the remainder of the plasmid. The first-codon in the BPI coding sequence and a codon for methionine in front of the BPI sequence were inserted through use of linker formed from two complementary annealed oligonucleotides, BPI-28: GACGCCACCATGGTC (SEQ ID NO: 13) and BPI-29: GACCATGGTGGCGTC (SEQ ID NO: 14). Those two oligonucleotides were ligated together with the HincII-SstII and SstII-HincII fragments from pIC124 to form pIC127.

Two plasmids, pML101 and pML102, were constructed using pIC127 for in vitro transcription/translation or rBPI(1–199)ala[132] and rBPI(1–199)ser[135]. To do this, pIC127 was digested with SstII and EcoRI and the large SstII-EcoRI fragment was purified. To construct pmL101, which contains an rBPI(1–199)ala[132] inset, the EcoRI-SstII fragment from pING4519 was ligated to the SstII-EcoRI fragment from PIC127. To construct pML102, which contains the rBPI (1–199)Ser[132] insert, the EcoRI-sstII fragment from pING4520 was ligated to the sstII-EcoRI fragment from pIC127.

rBPI(1–199), rBPI(1–199)Ser[135], and rBPI(1–199)ala[132] were expressed in vitro from plasmids pIC127, pML101, and pML102 using the TNT SP6 coupled Reticulocyte Lysate System from ProMega (Madison, Wisc.). That system allows in vitro coupled transcription and translation of cloned genes using a eukryotic translation system. Each coupled transcription/translation was carried out using the manufacturer's protocols with 2 µg of plasmid DNA in a total volume of 25 µl, including $^{35}$S-methionine to generate labeled protein. The protein products were added in 5 µl aliquots to a 20 µl urea sample buffer and heated at 95° C, for 3 minutes. Aliquots (10 µl) of each sample were run on a 15% SDS-Polyacrylamide gel either with or without DTT (50 mM). After fixing and drying the gel, the labeled protein bands were visualized by autoradiography. Results of the autoradiography demonstrate that cDNA encoding rBPI(1–199)ala[132], and rBPI(1–199)cys[135]

expressed protein products of the expected size of approximately 23 Kd for BPI N-terminal fragment. Moreover, all three expression products, rBPI(1-199), rBPI(-1-199)ala$^{132}$, and rBPI(1-199)cys$^{135}$, were capable of generating higher molecular weight species of the size expected for BPI(1-199) dimers, as well as larger species, all of which disappeared upon reduction with DTT. It is thought that the expression of dimeric species in the rBPI(1-199)cys$^{135}$ and rBPI(1-199)ala$^{132}$ products may be the result of using a cell-free in vitro transcription/translation system. Such a system does not allow proper post-translational processing, folding, etc. which would normally occur in cellular translation. Thus, it may be that proper disulfide linkages do not always form in the in vitro system, leading to formation of dimer in some cases.

Labeled proteins generated in the above-described in vitro expression system were next tested for LPS binding activity. Wells of microtiter plates were coated with LPS from *Salmonella minnesota* R7 (Rd mutant) (5 mg/ml in methanol stock culture) in 0.1M $Na_2CO_3$/20 mM EDTA (ethylenediamine tetraacetic acid) at pH 9.4 (a total of 2 μg LPS in a 50 μl well). Following overnight incubation at 4° C., the wells were rinsed with water and dried at 37° C. The wells were then blocked with 215 μl Dulbecco's-PBS/0.1% BSA for 3 hours at 37° C. The blocking solution was then discarded and the wells were washed with PBS/0.2 % Tween-20. The rBPI samples were then added (2 μl of the translation reactant) to a 50 μl total volume in PBS/0.2 % Tween. Following overnight incubation at 4° C., the wells were washed 3 times with PBS/0.2% Tween and the amount of labeled protein remaining in each well was determined by liquid scintillation counting. The results demonstrated that approximately equivalent LPS binding took place for all three BPI species referred to above. rBPI(1-199) displayed binding of 48,690 cpm; rBPI(-1-199)ala$^{132}$ displayed binding of 59,911 cpm; and rBPI(1-199)cys$^{135}$ displayed binding of 52,537 cpm. each of the aforementioned values represents the average of triplicate determinations. The average binding of the control (no DNA) was 5,395 cpm.

EXAMPLE 4

Product Characterization

A. Physical Characterization

Characterization of rBPI products was accomplished using reverse phase (C4) HPLC, cation exchange (MA7C) HPLC, SDS-PAGE, and electro-spray ionization mass spectrometry (ESI-MS). The rBPI products to be characterized were purified from roller bottles or from a 10 Liter fermenter harvest by either a single-step purification procedure or by a multi-step procedure. The single-step procedure was essentially that disclosed in co-pending, co-owned U.S. patent application Ser. No. 07/885,501 by Grinna, incorporated herein by reference, with the addition of a second wash step. In brief, S-sepharose beads were added to a growth medium containing rBPI products. The S-sepharose was then removed from the medium and washed with 20 mM sodium acetate and 100 mM sodium chloride at pH4.0. A second wash was performed with 20 mM sodium acetate and 700 mM sodium chloride at pH4.0. The purified rBPI products were eluted with 20 mM sodium acetate and 1000 mM sodium chloride at pH4.0.

The multi-step purification procedure involved the purification of pooled batches of rBPI products which had first been purified separately as described above. After purification of each of twenty individual rBPI product batches by the single-step method, the batches were pooled and repurified by first diluting the salt concentration of the pooled batches to 200 mM. The pooled sample was then loaded onto an S-sepharose column and was washed at pH4.0 with 20 mM sodium acetate, and 200 mM sodium chloride followed by 700 mM sodium chloride. The rBPI products were eluted using 20 mM sodium acetate and 1000 mM sodium chloride at pH4.0. The purified rBPI products were then analyzed to determine their physical characteristics.

1. SDS-PAGE Analysis of rBPI Products

SDS-PAGE analysis of rBPI products was carried out using 14% polyacrylamide gels and a tris-glycine buffer system under reducing and non-reducing conditions. Protein bands were stained with either Coomassie Blue or silver stain for visualization.

As shown in FIG. 1, non-reduced rBPI(1-199) appeared as a major band at approximately 23 kD and a minor band at approximately 40 kD. The major band was identified as rBPI(1-199) by comparison with simultaneously-run standards and the minor band was identified as a dimeric form of rBPI(1-199) by immunostaining. Upon addition of a 1/20 volume of 0.4M dithiothreitol (DDT) to a separate sample of rBPI(-1-199), SDS-PAGE revealed a single, well-defined band corresponding to the 23 kD monomeric species of rBPI(1-199) identified under non-reducing conditions as described above.

Figure 2A:
FIGS. 2A and 2B represents results of SDS-PAGE analysis of rBPI(1-193) and rBPI(1-199)ala$^{132}$ products.
Figure 2B:
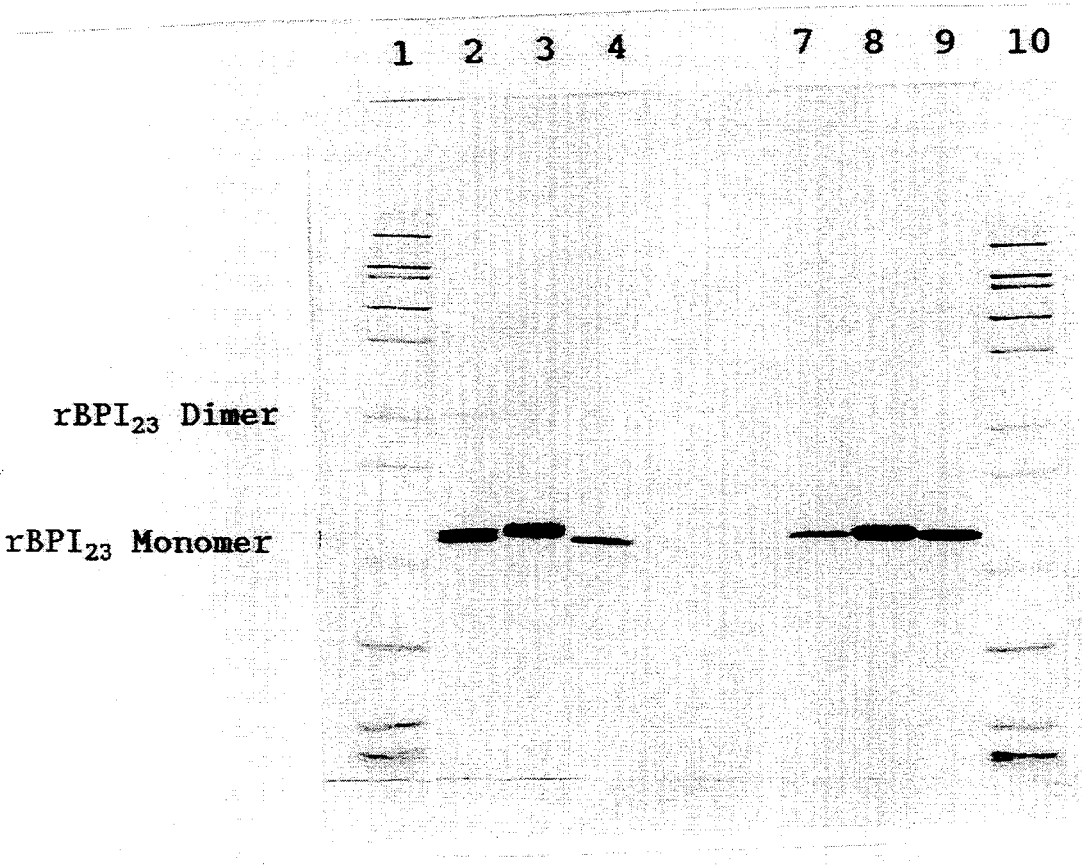

SDS-PAGE analysis of the rBPI(1-199)ala$^{132}$ product revealed a single band which migrated with the single 23 kD rBPI(1-199) band under reducing conditions. Under non-reduced conditions, rBPI(1-199)ala$^{132}$ migrated with the faster-migrating of the two closely-spaced bands seen for rBPI(1-199) (corresponding to the 23 kD band). These results, shown in FIGS. 2A and 2B, indicate that rBPI(1-199)ala$^{132}$ exists in essentially monomeric form after purification. Thus, rBPI products in which a cysteine residue is replaced by alanine display significant resistance to dimer formation.

2. Cation Exchange HPLC Analysis of rBPI Products

Cation exchange HPLC using an MA7C column was also employed to measure the dimer content of rBPI products. A Bio-Rad MA7C cartridge (4.6×30 mM, Bio-Rad Catalog No. 125-00556) equilibrated with 40% buffer B (20 mM MES, 1M NaCl, pH 5.5) at 1.0 ml/min was used. The rBPI(1-199) product was analyzed by diluting a 1 ml sample to 100 μg/ml and 200 μl of the diluted sample was injected onto the column. The rBPI was eluted with a gradient of 40% to 100% buffer B over 6 minutes. Buffer A comprised 20 mM MES at pH5.5. Absorbance was monitored at 229 nm.

Analysis of rBPI(1-199) revealed two peaks. A first peak eluted with a retention time of approximately 3 minutes as shown in FIG. 3. A second, smaller peak eluted at approximately 6 minutes. The first peak, shown in FIG. 3, represents rBPI(1-199) monomer and the second peak in FIG. 3 represents rBPI(1-199) dimer as determined by comparisons with the retention times of purified monomer and dimer standards. The second (dimer) peak did not appear when samples were reduced with DTT prior to being injected on the column.

Figure 4:
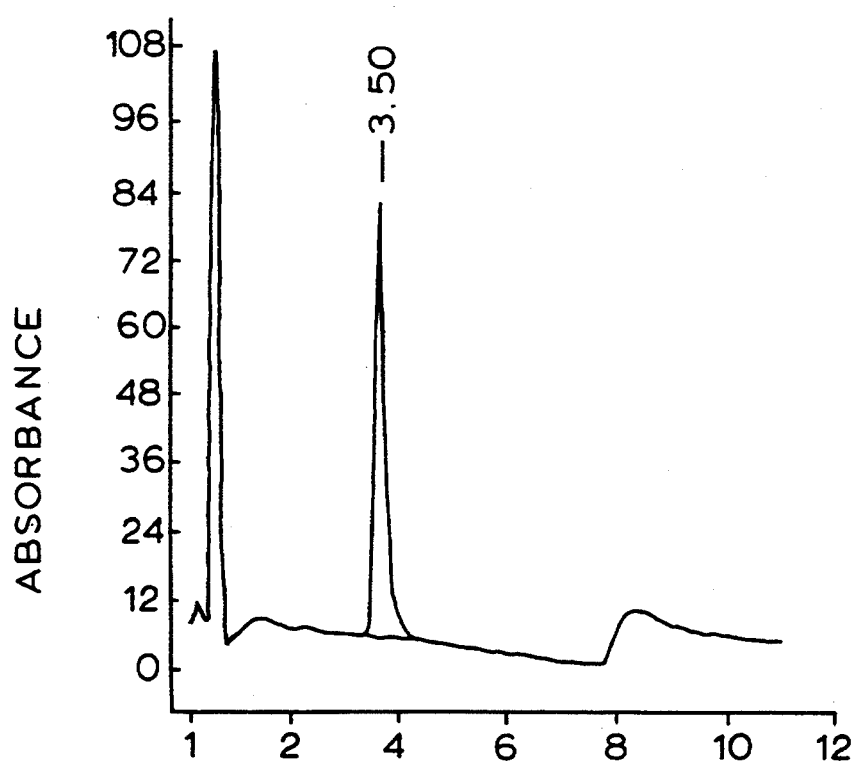
FIG. 4 shows results of cation exchange HPLC analysis of rBPI(1-199)ala$^{132}$ products.

Identical procedures were used to determine the elution pattern of rBPI(1-199)ala$^{132}$. As shown in FIG. 4, rBPI(1-199)ala$^{132}$ elutes as a single peak with a retention time corresponding to that observed for the rBPI(-

1-199) monomer peak. There was no evidence of dimer in the rBPI(1-199)ala¹³² sample.

3. Reverse Phase (C4) HPLC and Electrospray-ionization Mass Spectrometry Analysis of rBPI Products Microheterogeneity of rBPI products was revealed by reverse phase HPLC and electrospray-ionization mass spectrometry (ESI-MS). For the HPLC analysis, a Brownlee BU-300 C4 column was equilibrated with 37% Mobile Phase B (80% acetonitrile/0.065% TFA) at a flow rate of 0.5 ml/min. Samples (1 ml each) of rBPI(1-199) were diluted to 100 μg/ml and 50 μl of the sample was injected. The column was washed with 37% Mobile Phase B for 2.5 minutes and then eluted using a gradient from 37% to 50% Mobile Phase B over 20 minutes. Mobile Phase A was 5% acetonitrile/0.1% TFA and absorbance was monitored at 220 nm.

Figure 5:
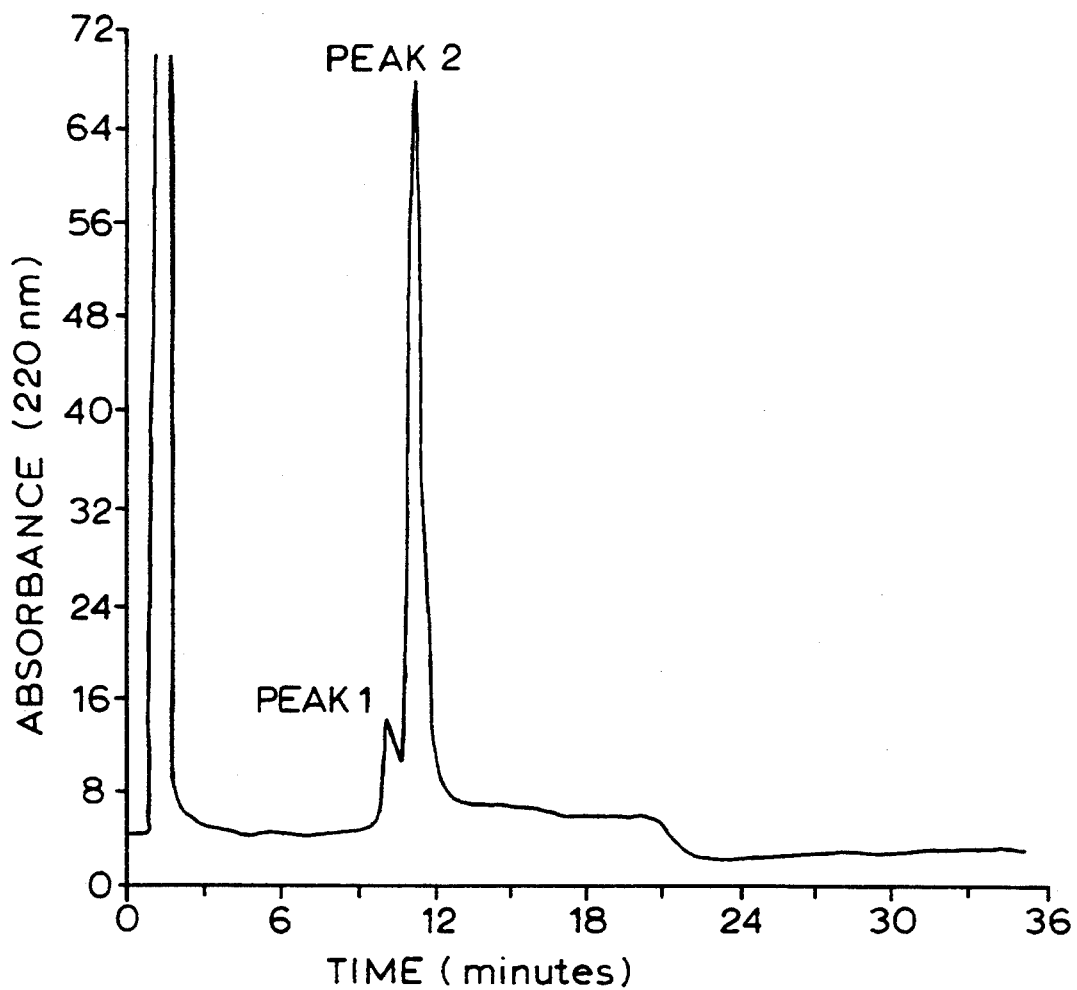
FIG. 5 represents results of reverse phase HPLC run on rBPI(1-199) products.

The results of reverse phase HPLC analysis of rBPI(1-199) products are shown in FIG. 5. rBPI(1-199) products elute as a second (major) peak with a partially-resolved first (minor) peak on the leading edge of the second peak. Upon reduction with DTT only one peak, corresponding to the second peak, elutes from the column.

Figure 6:
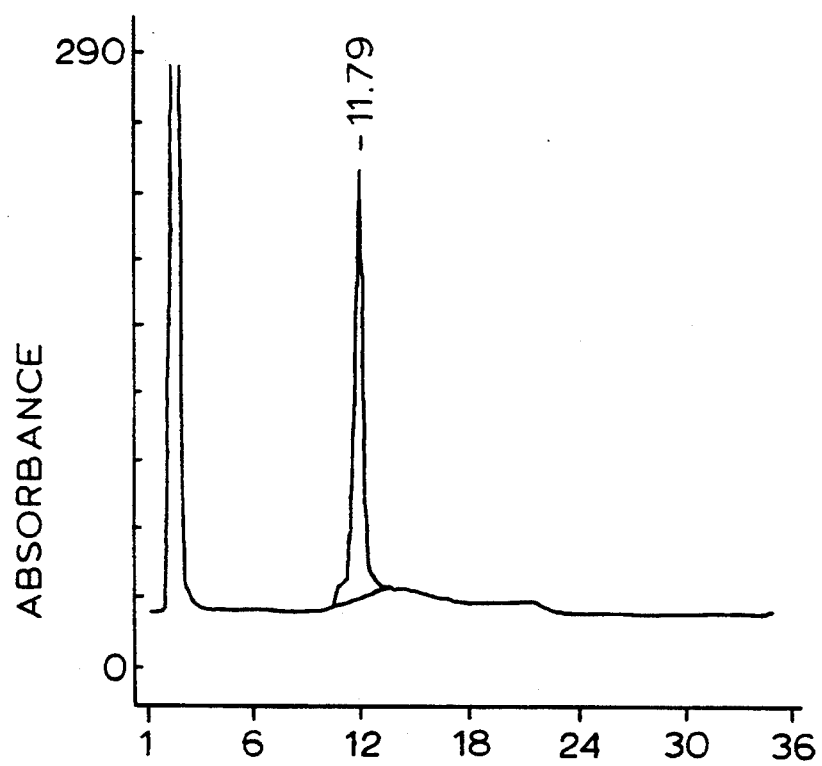
FIG. 6 represents results of reverse phase HPLC run on rBPI(1–199)ala$^{132}$ products.

Identical procedures were used to analyze rBPI(1-199)ala¹³² products. As shown in FIG. 6, rBPI(1-199)ala¹³² eluted as a single peak corresponding to the second (major) peak referred to above.

The eluates corresponding to the first and second HPLC peaks described above from three separate batches of rBPI(1-199) were isolated and analyzed to determine their content by ESI-MS. Analysis of the eluate which produced the second (major) peak from the rBPI(1-199) run revealed a slightly lower mass than would be expected for a 199-amino acid protein. These data indicate that the most abundant mass found in the second peak eluate corresponded to a 1-193 rBPI protein fragment. However, other species, ranging in size from 1-198 to 1-194, are also present. Analysis of the eluate producing the single peak obtained from HPLC on rBPI(1-199)ala¹³² revealed results similar to those obtained from the eluate which produced the second (major) peak above. These results are consistent with peptide mapping data which reveal truncated carboxy termini in rBPI(1-199) products.

When the same analysis was performed on rBPI(1-193) products, significantly reduced C-terminal heterogeneity was observed. The ESI-MS data obtained from rBPI(1-193) products revealed that approximately 85% of the protein contains either the first 191, 193, or 1.93 (+ an N-terminal alanine) amino acids of the BPI N-terminal. The results are shown in Table III.

TABLE III

Electrospray-Ionization Mass Spectrometry Results for rBPI(1-193) and rBPI(1-199) HPLC Monomer Peaks

| Expected rBPI Product | Approximate Molecular Mass | Predicted Amino Acid Residues | Approximate Relative Intensity* |
|---|---|---|---|
| rBPI(1-199) | 21407 | 1-193 | 50.9% |
|  | 21606 | 1-195 | 28.9% |
|  | 21505 | 1-194 | 20.1% |
|  | 21738 | 1-196 | <10% |
|  | 21846 | 1-197 | <10% |
|  | 21966 | 1-198 | <10% |
| rBPI(1-193) | 21408 | 1-193 | 36.2% |
|  | 21193 | 1-191 | 34.1% |
|  | 21293 | 1-192 | <10% |
|  | 21477 | 1-193 + N-terminal alanine | 14.5% |

TABLE III-continued

Electrospray-Ionization Mass Spectrometry Results for rBPI(1-193) and rBPI(1-199) HPLC Monomer Peaks

| Expected rBPI Product | Approximate Molecular Mass | Predicted Amino Acid Residues | Approximate Relative Intensity* |
|---|---|---|---|
|  | 20924 | 1-189 | 15.2% |

*Only species detected as being present in amounts greater than 10% were quantitated. These species were then normalized to 100%.

These data demonstrate that, while the rBPI(1-199)-encoding DNA produced no full-length (i.e. amino acids 1-199 of the BPI N-terminal) protein, the rBPI (1-193)-encoding DNA produced significant amounts of the rBPI(1-193) protein. Based upon these and other data, it appears that significant reductions in heterogeneity and significant increases in production of the intended protein (i.e. that for which the DNA insert codes may be obtained), while maintaining optimal bactericidal and LPS-binding activity, by using truncated forms of the rBPI-encoding DNA. It is expected that truncation of the DNA to be expressed will produce significant reductions in heterogeneity of the expression product to the extent that the DNA to be expressed is not truncated beyond the cysteine at amino acid residue 175. Expression products of truncated forms of DNA encoding rBPI proteins which have in the range of the first 176 amino acids of the BPI N-terminal to the first 193 amino acids of the BPI N-terminal are also expected to retain full bactericidal and LPS-binding activity.

The ESI-MS data also revealed the presence of microheterogeneity at the amino terminal of rBPI products. Forms of the rBPI product having an alanine residue at the amino terminus were found and confirmed by sequencing of tryptic peptides.

As shown in FIG. 5, the ESI-MS study of the eluate which produced the first (minor) reverse phase HPLC peak revealed proteins having a mass distribution similar to those which formed the second (major) peak except that each mass value was higher by approximately 119-120 Daltons. These data suggest that the eluate producing the first (minor) HPLC peak described above contains a disulfide-linked cysteine adduct, as this would account for the uniform shift of the mass values.

To test the hypothesis that the first (minor) reverse phase HPLC peak produced by rBPI(1-199) represents cysteine adducts, rBPI(1-199) was exposed to Ellman's reagent (dithionitrobenzenoic acid, DTNB) which binds to free sulfhydryl groups in roughly molar equivalents. Such treatment demonstrated that there is less than one mole of free sulfhydryl per mole of rBPI(1-199). Given the presence of three cysteine residues in BPI (at positions 132, 135 and 175), these results support the notion that there is either an intramolecular disulfide link in the rBPI products or that two of the sulfhydryl groups are sterically unavailable. rBPI(1-199)ala¹³² showed no reactivity with Ellman's reagent.

4. Storage Stability of rBPI(1-199) Products

Samples of rBPI(1-199) (1 mg/ml) in a buffer comprising 20 mM sodium citrate, 0.15M Sodium Chloride buffer, 0.1% poloxamer, and 0.002% polysorbate 80 at pH5.0 were analyzed to determine their storage stability over an 8-week period at the recommended storage temperature of 2°-8° C. and at higher temperatures of 22° C. and 37° C.

The results for storage at 2°-8° C., presented in Table IV, show an increase in the presence of dimer (from 1% to 4%), but no significant increase in cysteine adduct or particle formation in the sample.

sured every 2 minutes for 1 hour to determine the change in absorbance over time.

TABLE IV

| Storage Time | Appearance/ Color | pH | % Unknown Impurities | % Dimer by HPLC | Protein mg/mL | % Cysteine Adduct | LAL Inhibition IC$^{50}$,nG/mL | Particles/mL ≧10 μm | Particles/mL ≧25 μm |
|---|---|---|---|---|---|---|---|---|---|
| initial | clear/colorless | 5.1 | ND | 1.0 | 1.04 | 12 | 10 | 230 | 5 |
| 4 weeks | clear/colorless | 5.0 | ND | 3.2 | 1.02 | 11 | 11 | 113 | 2 |
| 8 weeks | clear/colorless | 5.0 | ND | 4.4 | 1.02 | 14 | 9 | 125 | 5 |

However, storage at the increased temperatures of 22° C. and 37° C. show that the presence of dimer and particles in the sample increased dramatically and the amount of cysteine adduct increased moderately. These results are shown in Table V. Additionally, when rBPI(1-193)ala$^{132}$ is stored at 22° C. to 37° C., no dimer was detected after storage for two weeks. Under similar conditions, rBPI(1-199) displays significant increases.

Figure 7:
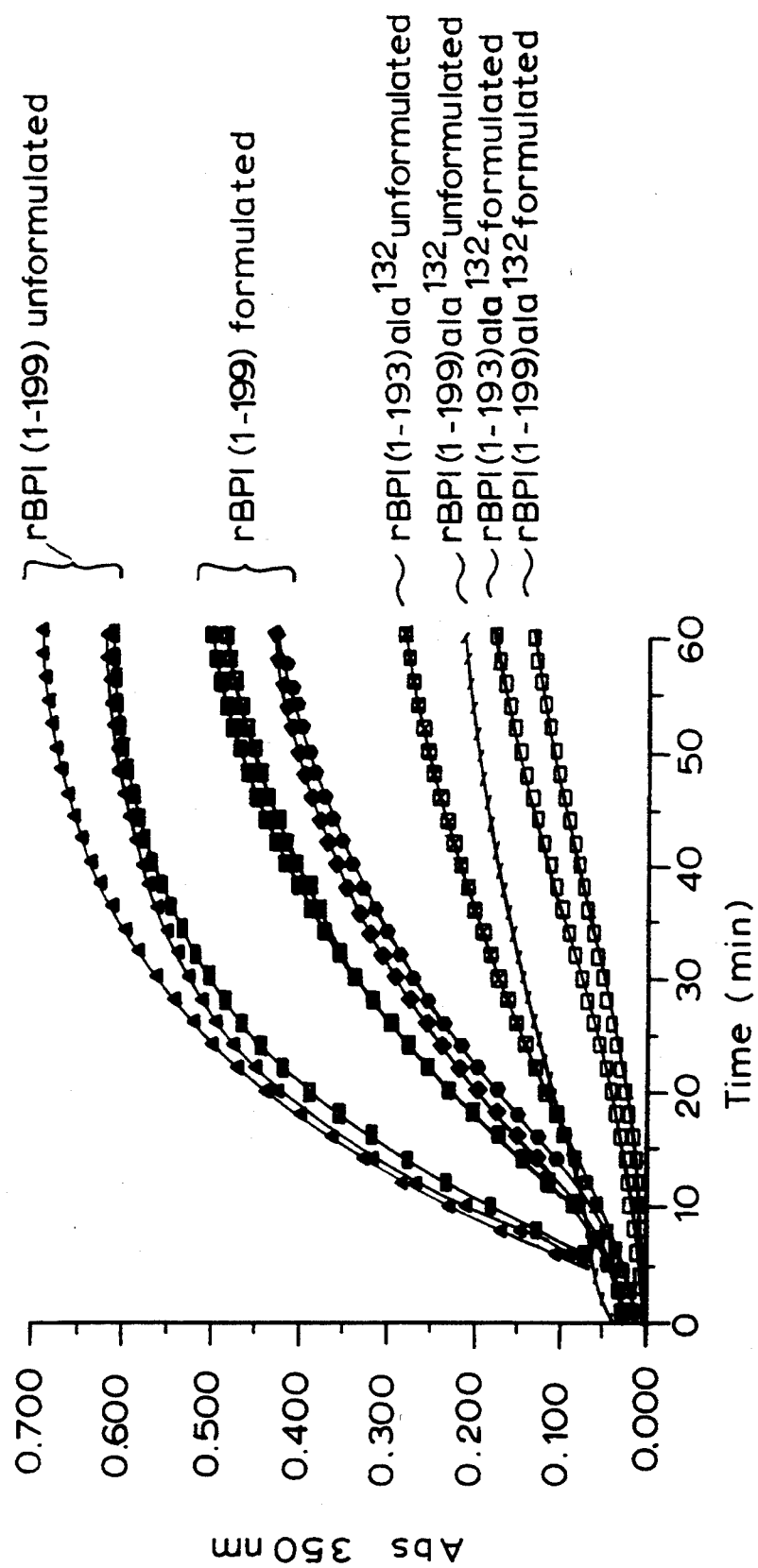
FIG. 7 presents results of turbidity studies on pharmaceutical compositions containing rBPI products with and without poloxamer/polysorbate surfactant ingredients at pH 7.0 and 57° C.

Results are presented in FIG. 7; wherein "formulated" refers to the rBPI product in citrate buffer containing the poloxamer/polysorbate combination referred to above, and "unformulated" refers to rBPI compounds in citrate buffer alone. A lower rate of change in turbidity (i.e., a lower rate of increase in absorbance over time) indicates increased stability against unfolding and the formation of particles. As

TABLE V

| Temperature | Storage Time | Appearance/ Color | pH | % Unknown Impurities | % Dimer by HPLC | Protein mg/mL | % Cysteine Adduct | LAL Inhibition IC$^{50}$,nG/mL | Particles/mL ≧10 μm | Particles/ mL ≧25 μm |
|---|---|---|---|---|---|---|---|---|---|---|
| | initial | clear/colorless | 5.1 | ND | 1.0 | 1.04 | 12 | 10 | 230 | 5 |
| 22° C. | 4 weeks | clear/colorless | 5.0 | ND | 4.5 | 1.02 | 12 | 10 | 100 | 4 |
| | 8 weeks | clear/colorless | 5.0 | ND | 6.8 | 1.02 | 14 | 6 | 126 | 3 |
| 37° C. | 4 weeks | a few particles | 5.0 | ND | 7.9 | 0.96 | 16 | 12 | 1,709 | 20 |
| | 8 weeks | numerous particles | 5.0 | ND | 13.1 | 0.88 | 18 | 7 | 20,287 | 611 |

5. Turbidity of rBPI Product Pharmaceutical Compositions

Experiments were done to determine the turbidity of various rBPI-containing pharmaceutical compositions. In this context, turbidity refers to the tendency of pharmaceutical compositions to engage in unfolding (i.e., loss of tertiary protein structure) and/or particle formation (interactions between individual proteins to form large (>10 μm) particles). The pharmaceutical compositions tested contained either rBPI(1-199), rBPI(1-199)ala$^{132}$, or rBPI(1-193)ala$^{132}$ in either a titrate buffer (20 mM sodium citrate/150 mM sodium chloride, pH 5.0) or a citrate buffer containing 0.1% poloxamer 188 (a poloxamer surfactant comprised of polyoxypropylene-polyoxyethylene block copolymer) and 0.002% polysorbate 80 (a polysorbate surfactant comprising polyoxyethylene sorbitan fatty acid ester). As mentioned above, use of a combination poloxamer/polysorbate surfactant system stabilizes pharmaceutical compositions as taught in co-owned, co-pending U.S. patent application Ser. No. 08/012,360, filed on Feb. 2, 1993 by McGregor et al., incoporated herein by reference.

Samples were analyzed to determine their resistance to turbidity over time at increasing temperature and at either pH 7.0 or pH 5.0. Prior to analysis, all samples were diluted to a concentration of 0.1 mg/ml in either 50 mM potassium phosphate or 20 mM citrate buffer at pH 7.0. Turbidity measurements were obtained by placing samples in quartz cuvettes for use in a Shimadzu UV-160 UV-Vis spectrophotometer (Shimadzu, Pleasanton, Calif.) equipped with a temperature-controlled cuvette holder attached to a recirculating water bath. Upon equilibrating the cuvette holder at the desired temperature (57° C., 65° C., or 85° C., see below), absorbance at 280 nm was measured to confirm that samples had been diluted to the proper concentration. Following this, the absorbance of samples at 350 nm was meashown in FIG. 7, the addition of the aforementioned combination of surfactants resulted in increased stability (resistance to particle formation and unfolding) of all compositions tested. Moreover, the rBPI(1-199)ala$^{132}$ and rBPI(1-193)ala$^{132}$ exhibited greatly improved resistance to unfolding and particle formation relative to wild-type compositions—regardless of whether the surfactant combination was present. Similar results were obtained at pH 5.0 and 65° C., at pH 5.0 and 75° C. and at 85° C., respectively.

Overall, compositions with the surfactant combination and/or the cysteine deletion showed greatly increased stability over time and through increases in temperature as compared to compositions with no surfactant and/or having the wild type BPI(1-199) N-terminal construction.

B. In Vitro Activity Characterizations

In Vitro activity of rBPI(1-199)ala$^{132}$ products was determined by binding of the products to LPS, by the LAL inhibition assay, and by the bactericidal potency of the products.

1. Binding Of rBPI(1-199)ala$^{132}$ To LPS

Samples (20 μg to 60 μg each) of *E. coli* (Strain 011 1-B4) or *S. minnesota* (Rd mutant) lipopolysaccharide (Sigma Chemical, St. Louis, Mo.) were used to determine the ability rBPI(1-199)ala$^{132}$ products to bind LPS.

The LPS samples were size fractionated by SDS-PAGE and silver stained for visualization or electrotransferred to a nitrocellulose membrane (BA25, Schleicher and Schuell, Keene, N.M.) with appropriate pre-stain standards. The LPS blots were processed by soaking the membrane in 50 mM Tris, 0.2M NaCl (TBS), and 30 mg/ml bovine serum albumin (BSA) at pH 7.4 for 30 minutes at 37° C. Membranes were then incubated in a solution containing 2-4 μg of purified or partially purified rBPI(1-199)ala$^{132}$ or a control protein (either rBPI(1-199) or rBPI holoprotein) for 12-18 hours at 21° C. to 42° C. After incubation, the membranes were then washed with TBS-BSA. The solution was changed at least three times over a 30 minute period. The washed membranes were then incubated for 3 hours in a 1:1000 dilution of rabbit anti-rBPI(1-199) in TBS containing 1 mg/ml BSA. Membranes were next washed at least three times and were developed using the Chemiluminescent Detection System (Tropix Systems, Bedford, Mass.) according to the manufacturers instructions, using 5×PBS and 0.25% gelatin (Bio-Rad) in place of I-block.

The results, shown in FIG. 11, demonstrate that rBPI(1-199)ala$^{132}$ binds to LPS fixed to nitrocellulose as well or better than rBPI(1-199).

2. *E. coil* Growth Inhibition Assay

The *E. coli* broth growth inhibition assay was conducted to determine the bactericidal potency of rBPI products by treating *E. coli* with rBPI(1-199) or rBPI(1-199)ala$^{132}$ analogs and monitoring the inhibition of broth growth as a measure of bactericidal activity. A "rough" strain of *E. coli* with short-chain LPS, designated J5 (a rough UDP-4-epimerase-less mutant of *E. coli* strain 0111:B4), was used in the assay. Cells were grown in a triethanolamine-buffered mineral salts medium (Simon, et al. *Proc. Nat. Acad Sci,* 51:877 (1964)) which rendered *E. coli* especially sensitive to BPI. The cells were washed and resuspended in 0.9% NaCl to a density of about $5 \times 10^8$ cells/ml.

Approximately $5 \times 10^6$ to $1 \times 10^7$ *E. coli* cells were incubated for 30-60 minutes with either rBPI(1-199) or with rBPI(1-199)ala$^{132}$ analogs at a concentration of 5 µg/ml with a buffered solution (10% Hanks Balanced Salts, 40 mM Tris-Hcl, pH 7.5. 0.1% casamino acids) in a volume of 200-400 ml. In addition, the assay was run separately with either rBPI(1-199) or rBPI(1-199)ala$^{132}$ analog and 100 mM MgCl$_2$. Following incubation, the cells were diluted with 10 volumes of nutrient broth supplemented with 0.9% Nacl. Broth growth was then monitored for several hours.

The results, shown in FIG. 12, demonstrate that rBPI(1-199)ala$^{132}$ analogs possess bactericidal activity as potent or more potent than rBPI(1-199). The bactericidal activity of both rBPI(1-199)ala$^{132}$ analogs and that of rBPI(1-199) were reduced, as expected, by MgCl$_2$.

3. LAL Inhibition Assay

The LAL inhibition assay was used to determine the ability of rBPI(1-193)ala$^{132}$ to bind LPS. An LAL inhibition assay is described in Gazzano-Santoro, *Infect. Immun.*, 60:4754-4761 (1992). Results of the LAL assay demonstrate that rBPI(1-193)ala$^{132}$ has an IC-50 value of 10, which is equal to that for rBPI(1-199). These data indicate that the analog competes as well as the wild-type rBPI product for binding to LPS.

C. Efficacy Of rBPI(1-199)ala$^{132}$ In An Animal Model Of Lethal Endotoxemia

An animal model of endotoxemia was used to evaluate the comparative effectiveness of rBPI(1-199)ala$^{132}$ and rBPI(1-199) against endotoxic shock.

Male ICR mice received intravenous injections of 800 µg/kg actinomycin-D and either 0.5 µg/kg or 1.0 µg/kg of an endotoxin (*E. coli,* Strain 0111:B4). Immediately following the injection of endotoxin, the mice received an intravenous injection (0.5 mg/kg or 5.0 mg/kg) of either rBPI(1-199) or rBPI(1-199)ala$^{132}$. Buffered vehicle was used as a control. Deaths were then recorded over a 7-day period. The results are presented below in Table VI.

TABLE VI

|  | BPI Dose | # Dead/Total | % Mortality |
| --- | --- | --- | --- |
| Buffer only | 0 | 14/15 | 93 |
| rBPI$_{23}$ | 0.5 mg/kg | 7/15 | 47 |
|  | 5.0 mg/kg | 8/15 | 53 |
| rBPI$_{23}$-cys | 0.5 mg/kg | 14/15 | 93 |
|  | 5.0 mg/kg | 8/16 | 50 |

As seen in Table VI, both rBPI(1-199)ala$^{132}$ and rBPI(1-199) provided significant protection against the lethal effects of the endotoxin. Although the present invention has been presented in terms of its preferred embodiments, the skilled artisan realizes that numerous modifications and substitutions are within the scope of the present teaching. For example, substitution of the cysteine at position 132 or 135 of the BPI N-terminal fragment with non-polar amino acids other than alanine or serine is contemplated by the invention. Thus, the scope of the appended claims and any future amendments thereto.

---

We claim:

1. A polypeptide analog of human bactericidal/-permeability-increasing protein wherein a cysteine residue at position 132 is replaced by a different amino acid.

2. The polypeptide analog of claim 1 wherein the amino acid replacing said cysteine residue is a non-polar amino acid selected from the group consisting of alanine and serine.

3. The polypeptide analog of claim 1 wherein the cysteine residue at position 132 is replaced by alanine.

4. The polypeptide analog according to claims 1, 2, or 3 comprising from 176 to 199 residues from the amino-terminus of human bactericidal/permeability-increasing protein.

5. The polypeptide analog according to claim 4 comprising the initial 193 amino terminal amino acid residues of human bactericidal/permeability-increasing protein.

6. A DNA encoding a polypeptide analog of human bactericidal/permeability-increasing protein wherein a cysteine residue at position 132 is replaced by a different amino acid.

7. The DNA of claim 6 encoding the thirty-one amino acid leader sequence and the first 193 N-terminal residues of human bactericidal/permeability-increasing protein and having a stop codon immediately following the codon for the leucine residue at position 193.

8. The DNA of claim 6 encoding the thirty-one amino acid leader sequence and the first 199 N-terminal residues of human bactericidal/permeability-increasing protein and having a stop codon immediately following the codon for the isoleucine at position 199.

9. An autonomously replicating DNA vector comprising a DNA according to claim 6.

10. A host cell culture stably transformed or transfected with DNA according to claim 6 in a manner allowing expression in said host cell culture of said polypeptide analog.

11. A eukaryotic host cell culture according to claim 10.

12. A host cell culture according to claim 11 wherein the host cell culture comprises a host cell line selected from the group consisting of ATCC CRL 11246 and ATCC HB11247.

13. A method for producing a polypeptide analog of human bactericidal/permeability-increasing protein comprising growing a host cell culture according to claim 10 in a suitable culture medium and isolating said polypeptide analog from said host cell culture or said culture medium.

14. A DNA encoding a biologically active fragment of human bactericidal/permeability-increasing protein having a leucine residue at position 193 as its carboxy terminal residue.

15. The DNA according to claim 14 encoding the thirty-one amino acid leader sequence and first 193 N-terminal amino acids of human bactericidal/permeability-increasing protein and having a stop codon immediately following the codon for the leucine residue at position 193.

16. An autonomously replicating DNA vector comprising a DNA according to claim 14.

17. A host cell culture stably transformed or transfected with a DNA according to claim 14 in manner allowing expression in said host cell culture.

18. A method for producing a biologically active human bactericidal/permeability-increasing protein fragment comprising growing a host cell culture stably transformed or transfected with DNA according to claim 14 in a suitable culture medium and isolating said fragment from said host cell culture or said culture medium.

19. A DNA encoding a polypeptide analog according to claim 4.

* * * * *

UNITED STATES PATENT AND TRADEMARK OFFICE
CERTIFICATE OF CORRECTION

PATENT NO.: 5,420,019            Page 1 of 2

DATED: May 30, 1995

INVENTOR(S): Georgia Theofan, Arnold Horwitz, David Burke, Manik Baltaian and Lynn Grinna It is certified that error appears in the above-identified patent and that said Letters Patent is hereby corrected as shown below:

Col. 6, line 19, "Sail" should be --SalI--.

Col. 8, line 50, "BglII" should be --BglII--.

Col. 9, line 15, "pING4 150" should be --pING4150--.

Col. 9, line 26, "neogene" should be --neo gene--.

Col. 9, line 42, "pING 4 150" should be --pING4150--.

Col. 10, line 7, "pING 4 144" should be --pING4144--.

Col. 10, line 16, "pING 4 145" should be --pING4145--; "pING4 148" should be -- pING4148--; and pING4 152 should be --pING4152--.

Col. 10, line 18 "pING4 150" should be --pING4150--.

Col. 10, line 33 "pING4 148" should be --pING4148--.

UNITED STATES PATENT AND TRADEMARK OFFICE
CERTIFICATE OF CORRECTION

PATENT NO. : 5,420,019

DATED : May 30, 1995

INVENTOR(S) : Georgia Theofan, Arnold Horwitz, David Burke, Manik Baltaian and Lynn Grinna It is certified that error appears in the above-identified patent and that said Letters Patent is hereby corrected as shown below:

Col. 16, line 36 "pING4 143" should be --pING4143--.

Col. 20, line 61 "The protein" should be --The labeled protein--.

Col. 23, line 52 "1.93" should be --193--.

Col. 25, line 42 "titrate" should be --citrate--.

Col. 25 line 53 "incoporated" should be --incorporated--.

Col. 27, line 13 delete "shown in FIG. 11,"

Col. 27, line 41 delete "shown in FIG. 12,"

Signed and Sealed this

Thirteenth Day of August, 1996

Attest:

BRUCE LEHMAN

*Attesting Officer*    *Commissioner of Patents and Trademarks*